Figure 1:
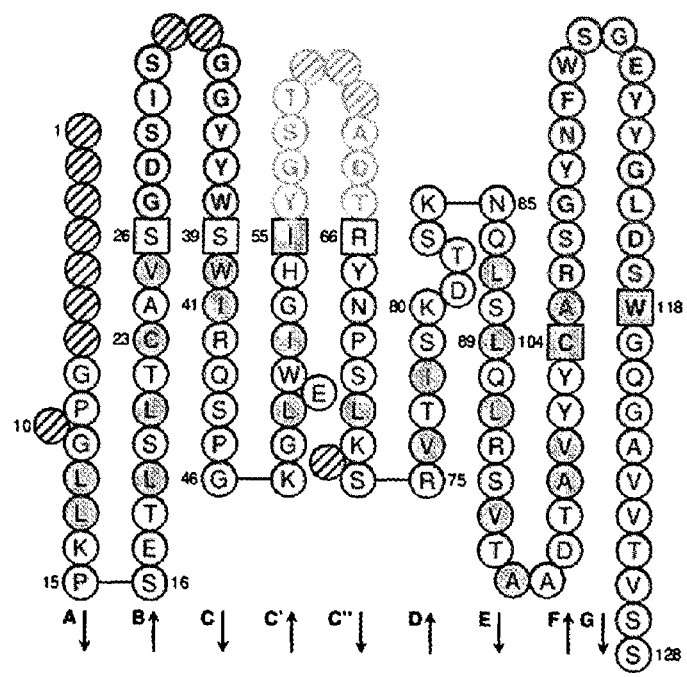
Figure 1:
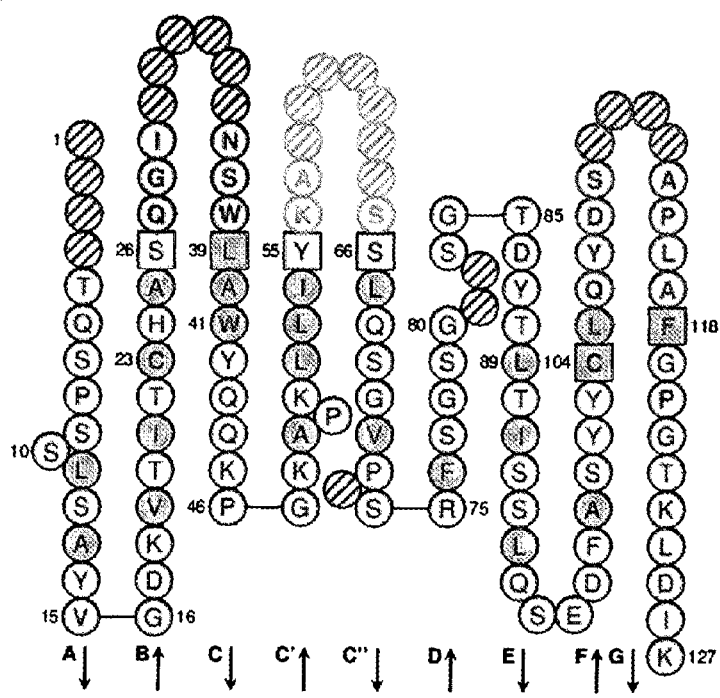

US010059760B2

(12) United States Patent
Behrens et al.

(10) Patent No.: US 10,059,760 B2
(45) Date of Patent: Aug. 28, 2018

(54) IMMUNOGLOBULIN AGAINST THE ANTHRAX TOXIN

(71) Applicants: LABORATOIRE FRANCAIS DU FRACTIONNEMENT ET DES BIOTECHNOLOGIES, Les Ulis (FR); ETAT FRANCAIS REPRESENTE PAR LE DIRECTEUR CENTRAL DU SERVICE DE SANTE DES ARMEES, Armees (FR)

(72) Inventors: Christian Behrens, Vauhallan (FR); Philippe Klein, Ales (FR); Denis Hoguet, Saint Hilaire de Brethmas (FR)

(73) Assignees: LABORATOIRE FRANCAIS DU FRACTIONNEMENT ET DES BIOTECHNOLOGIES, Les Ulis (FR); ETAT FRANCAIS REPRESENTE PAR LE DIRECTEUR CENTRAL DU SERVICE DE SANTE DES ARMEES, Armees (FR)

( * ) Notice: Subject to any disclaimer, the term of this patent is extended or adjusted under 35 U.S.C. 154(b) by 0 days.

(21) Appl. No.: 15/111,256

(22) PCT Filed: Jan. 16, 2015

(86) PCT No.: PCT/FR2015/050113
§ 371 (c)(1),
(2) Date: Jul. 13, 2016

(87) PCT Pub. No.: WO2015/107307
PCT Pub. Date: Jul. 23, 2015

(65) Prior Publication Data

US 2016/0347830 A1 Dec. 1, 2016

(30) Foreign Application Priority Data

Jan. 17, 2014 (FR) ..................................... 14 50405

(51) Int. Cl.

| | |
|---|---|
| *C07K 16/12* | (2006.01) |
| *G01N 33/569* | (2006.01) |
| *A61K 47/10* | (2017.01) |
| *A61K 39/40* | (2006.01) |
| *A61K 47/68* | (2017.01) |
| *A61K 39/00* | (2006.01) |

(52) U.S. Cl.

CPC .......... *C07K 16/1278* (2013.01); *A61K 39/40* (2013.01); *A61K 47/6835* (2017.08); *G01N 33/56911* (2013.01); *A61K 2039/505* (2013.01); *A61K 2039/545* (2013.01); *C07K 2317/21* (2013.01); *C07K 2317/24* (2013.01); *C07K 2317/41* (2013.01); *C07K 2317/76* (2013.01); *C07K 2317/92* (2013.01); *G01N 2333/32* (2013.01)

(58) Field of Classification Search
None
See application file for complete search history.

(56) References Cited

U.S. PATENT DOCUMENTS

| | | | | |
|---|---|---|---|---|
| 8,507,655 B2 * | 8/2013 | Thullier ............ | C07K 16/1278 530/387.3 |
| 2006/0121045 A1 | 6/2006 | Iverson et al. | |

FOREIGN PATENT DOCUMENTS

| | | |
|---|---|---|
| WO | WO 2009/050388 A2 | 4/2009 |
| WO | WO 2009/071860 A2 | 6/2009 |

OTHER PUBLICATIONS

Skolnick et al. (Trends in Biotechnology 18: 34-39, 2000).*
Greenspan et al. (Nature Biotechnology 7: 936-937, 1999).*
Giusti et al. (Proc. Natl. Acad. Sci. USA. May 1987; 84 (9): 2926-2930).*
Winkler et al (J. Imm., 265:4505-4514, 2000).*
Chien et al. (Proc. Natl. Acad. Sci. USA. Jul. 1989; 86 (14): 5532-5536).*
Caldas et al. (Mol. Immunol. May 2003; 39 (15): 941-952).*
Casadevall et al. (PNAS, vol. 109 No. 31, pp. 12272-12273).*
Laffly et al., "Selection of a macaque Fab with framework regions like those in humans, high affinity, and ability to neutralize the protective antigen (PA) of Bacillus anthracis by binding to the segment of PA between residues 686 and 694," Antimicrobial Agents and Chemotherapy, vol. 49, No. 8, pp. 3414-3420, Aug. 2005.
Laffly et al., "Improvement of an Antibody Neutralizing the Anthrax Toxin by Simultaneous Mutagenesis of Its Six Hypervariable Loops," Journal of Molecular Biology, vol. 378, No. 5, pp. 1094-1103, May 2008.

(Continued)

*Primary Examiner* — Robert A Zeman
(74) *Attorney, Agent, or Firm* — Potomac Law Group, PLLC

(57) ABSTRACT

The present invention relates to a class-G immunoglobulin against the anthrax toxin protective antigen (PA), or one of the fragments of same, comprising at least: a variable heavy-chain region comprising an amino acid sequence represented by the sequence SEQ ID NO: 1, or comprising an amino acid sequence having at least 90% identity with the sequence SEQ ID NO: 1, and comprising the amino acids Leucine in position 51 and Glycine in position 67, and a variable light-chain region comprising an amino acid sequence represented by the sequence SEQ ID NO: 2, or comprising an amino acid sequence having at least 90% identity with the sequence SEQ ID NO: 2, and comprising a Leucine amino acid in position 55. The invention also relates to the uses of such an immunoglobulin.

8 Claims, 3 Drawing Sheets

Specification includes a Sequence Listing.

(56) References Cited

OTHER PUBLICATIONS

Presta et al., "Engineering of therapeutic antibodies to minimize immunogenicity and optimize function," Advanced Drug Delivery Reviews, vol. 58, No. 5-6, pp. 640-656, Aug. 2006.
Wark et al., "Latest technologies for the enhancement of antibody affinity," vol. 58, No. 506, Advanced Drug Delivery Reviews, vol. 58, No. 5-6, pp. 657-670, Aug. 2006.
International Search Report issued in application No. PCT/FR2015/050113 dated Apr. 23, 2015.

* cited by examiner

A) VH 6.20

B) VL 6.20

IMMUNOGLOBULIN AGAINST THE ANTHRAX TOXIN

The present invention relates to an immunoglobulin directed against the anthrax toxin protective antigen.

Anthrax is an infectious disease caused by a gram-positive bacterium, *Bacillus anthracis*. This bacterium is non-mobile and forms highly resistant spores which germinate into a vegetative form when they are in environments such as human or animal blood or tissues. Despite their high resistance, the spores do not reproduce; on the other hand, they can survive tens of years in the soil.

An anthrax infection can take three forms: cutaneous, pulmonary or gastrointestinal. The pulmonary infection is usually lethal. In the event of inhalation, the *B. anthracis* spores pass into the alveoli where they are phagocytosed by macrophages and dendritic cells, in particular. The spores germinate in these cells and the vegetative forms multiply in the lymph nodes. The bacteria then pass into the blood, reproduce continually and produce toxins which are partly responsible for the lethality of the disease.

Anthrax toxins are composed of three distinct proteins: the protective antigen (PA, 83 kDa before enzymatic cleavage and 63 kDa after cleavage), the lethal factor (LF, 90 kDa) and the edema factor (EF, 89 kDa). The lethal toxin, which plays a predominant role in the pathogenicity, is made up of PA and LF; and the edema toxin, which has a lesser role in the physiology of the disease, is made up of PA and EF. These proteins are secreted by the bacterium as non-toxic monomers, and assemble at the surface of the target cells to form toxic complexes.

Up until now, several antibiotics, such as penicillin, doxycycline and fluoroquinolones (for example ciprofloxacin), have been used for the treatment of anthrax infections. However, some of these antibiotics may not have effects on certain antibiotic-resistant strains of *B. anthracis*. Furthermore, since antibiotics do not have inhibitory action with respect to anthrax toxins, they must necessarily be administered at very early stages in the infection; however, early diagnostics are difficult to establish since the initial symptoms are nonspecific.

Vaccines, the major component of which is the protective antigen PA, have been developed but are used only for individuals who may be in contact with *B. anthracis*. Furthermore, because of the need for a period of several months in order to acquire sufficient immunity, these vaccines cannot be used in emergency situations. In France currently, none of these vaccines is approved for human use. It is therefore necessary to develop new therapeutic and preventive approaches, other than antibiotics.

Passive immunization with antibodies represents an effective strategy for neutralizing the toxin. Several trials have been carried out to neutralize the anthrax lethal toxin using monoclonal antibodies against the protective antigen (PA) and the lethal factor (LF). The neutralization of the anthrax lethal toxin using an antibody may take place by inhibition of the binding of PA to its cell receptor, inhibition of PA cleavage, inhibition of the binding between PA and LF or else inhibition of the action of LF for example. The development of novel antibodies for neutralizing the anthrax toxin is thus of general interest for effective prevention and treatment of anthrax.

In a recent study, a macaque was immunized with the protective antigen PA83 in order to obtain antibodies intended to treat human infection with anthrax. Using the bone marrow, the genes encoding Fab antibody fragments specifically recognizing PA83 were amplified and cloned in order to obtain a fragment library.

A high-affinity fragment (Kd=3.4 nM) which effectively neutralizes the lethal toxin (50% inhibitory concentration=5.6+/−0.13 nM), denoted by the name 35PA83, was then isolated (Laffly et al., antimicrobial agents and chemotherapy, 2005, 49(8): 3414-3420). The 35PA83 immunoglobulin fragment neutralizes the anthrax toxin by preventing the interaction of PA with its cell receptor.

A chimeric immunoglobulin of 35PA83, called "v2", the variable regions of which are derived from the 35PA83 fragment, was prepared and described in international application WO 2009/071860.

Nevertheless, the increase in the affinity of this immunoglobulin fragment with respect to the PA antigen appears to have the double advantage of reducing the amount of immunoglobulin to be administered to the patient and of reducing the costs of the treatment, but also that of allowing better detection of the anthrax toxin.

One of the aims of the invention is thus to provide an immunoglobulin which has a high affinity with respect to the anthrax toxin PA antigen, and which allows very sensitive detection of the anthrax toxin.

Another aim of the invention is to provide an immunoglobulin which allows the treatment or prevention of pathological conditions associated with the anthrax toxin.

Another aim of the invention is to provide a method for detecting the anthrax toxin.

Yet another aim of the invention is also to provide a kit for detecting the anthrax toxin.

A subject of the present invention is thus a class-G immunoglobulin directed against the anthrax toxin protective antigen, or a fragment thereof, comprising at least:
- a heavy-chain variable region comprising an amino acid sequence having at least 90% identity with the sequence SEQ ID No.: 1, it being understood that it comprises the amino acids leucine in position 51 and glycine in position 67, and/or
- a light-chain variable region comprising an amino acid sequence having at least 90% identity with the sequence SEQ ID No.: 2, it being understood that it comprises the leucine amino acid in position 55.

The sequence SEQ ID No.: 1 comprises a leucine in position 51 and a glycine in position 67. The sequence SEQ ID No.: 2 comprises a leucine in position 55. The sequences according to the invention have at least 90% identity with SEQ ID No.: 1 or 2, but necessarily contain, as appropriate, leucine in position 51 and glycine in position 67 (SEQ ID No.: 1), or leucine in position 55 (SEQ ID No.: 2).

Preferably, the immunoglobulin or a fragment thereof according to the invention has an affinity for the anthrax toxin protective antigen of less than $3.4 \times 10^{-9}$ M, preferably less than $3 \times 10^{-9}$ M, preferably less than or equal to $2.5 \times 10^{-9}$ M, preferably less than $2 \times 10^{-9}$ M, preferably less than $1.5 \times 10^{-9}$ M, preferably less than $1 \times 10^{-9}$ M, preferably less than or equal to $3.3 \times 10^{-11}$ M.

The term "immunoglobulin" is equivalent to the term "antibody", i.e. it refers to a multimeric protein consisting of 4 chains participating in the acquired immune response.

The term "immunoglobulin fragment" is intended to mean a fragment which has the capacity to bind to the PA antigen. Preferably, such a fragment comprises at least:
- a heavy-chain variable region comprising an amino acid sequence represented by the sequence SEQ ID No.: 1, and/or
- a light-chain variable region comprising an amino acid sequence represented by the sequence SEQ ID No.: 2.

Thus, firstly, it is possible to use an immunoglobulin of the invention, i.e. a whole immunoglobulin molecule, i.e. an immunoglobulin consisting of two complete heavy chains and two complete light chains. Secondly, an immunoglobulin fragment according to the invention can be used. Well-known immunoglobulin fragments are, for example, F(ab')2, Fab, Fv, scFv and Fd fragments.

Type-G immunoglobulins (IgG) are heterodimers consisting of 2 heavy chains and 2 light chains, linked to one another by disulfide bridges. Each chain consists, in the N-terminal position, of a variable region or domain (encoded by the rearranged genes V-J for the light chain and V-D-J for the heavy chain) specific for the antigen against which the immunoglobulin is directed, and, in the C-terminal position, of a constant region, consisting of a single CL domain for the light chain or of 3 domains (CH1, CH2 and CH3) for the heavy chain.

The combination of the variable domains and of the CH1 and CL domains of the heavy and light chains forms the Fab parts, which are connected to the Fc region by a very flexible hinge region allowing each Fab to bind to its antigen target, while the Fc region, which mediates the effective properties of the antibody, remains accessible to the immune effectors, phagocytes or killer cells, and complement; these constant regions are not involved in antigen binding.

The Fc region, consisting of the 2 globular domains CH2 and CH3, is glycosylated on the CH2 domain, with the presence, on each of the 2 chains, of a biantennary N-glycan, bonded to the asparagine in position 297 of the heavy-chain sequence of the antibodies according to the EU numbering (Asn 297—cf. Edelman, G. M. et al., Proc. Natl. Acad. USA, 63, 78-85 (1969), and IMGT web site www.imgt.org/IMGTScientificChart/Numbering/Hu_IGH-Gnber.html In the present application, the term "Asn 297" is intended to mean in reality asparagine in position 305 of the sequence SEQ ID No.: 5.

The variable region is, for its part, involved in the binding of the immunoglobulin to its epitope.

An immunoglobulin of which the constant region (Fc) has been enzymatically cleaved, so as to preserve the hinge region thereof, is denoted as an F(ab')2 fragment and retains the two antigen-binding sites.

Likewise, an immunoglobulin of which the constant region, including the hinge region, has been enzymatically cleaved, or which has been produced without this region, is denoted as a Fab fragment and retains one of the two antigen-binding sites.

The Fd fragment is formed from the VH and CH1 regions.

Located in the variable region are the complementarity determining regions (CDRs), also called hypervariable regions, which interact directly with the antigen and therefore have a determining impact on the affinity of an antibody for its antigenic target.

Located in the variable region are regions of a second type, called framework regions (FRs), which maintain the tertiary structure of the CDRs. These framework regions are relatively specific for the species in which the immunoglobulin has been produced. Located in the Fd fragment of the heavy chain and in the light chain are four framework regions (FR1 to 4) separated respectively by three CDRs (CDR1 to 3).

According to the invention, a sequence having at least 90% identity with a reference sequence has at least 90%, preferably at least 91%, 92%, 93%, 94%, 95%, 96%, 97%, 98% or 99%, amino acid identity with said reference sequence.

The "percentage identity" between two sequences, for the purposes of the present invention, is determined by comparing the two optimally aligned sequences through a comparison window. The part of the amino acid sequence in the comparison window may thus comprise additions or deletions (for example "gaps") compared with the reference sequence (which would not comprise these additions or these deletions) so as to obtain an optimal alignment between the two sequences.

The percentage identity is calculated by determining the number of positions for which an amino acid residue is identical in the two sequences compared, then by dividing the number of positions for which there is identity between the two amino acid residues, by the total number of positions in the comparison window, then by multiplying the result by one hundred in order to obtain the percentage amino acid identity of the two sequences with respect to one another.

The invention is based on the surprising observation made by the inventors that the combination of a specific double mutation of the heavy chain (which results in a leucine in position 51 and in a glycine in position 67 in SEQ ID No.: 1) and a specific mutation of the light chain (which results in a leucine in position 55 in SEQ ID No.: 2) leads to a better affinity of 35PA83 immunoglobulin with respect to the anthrax toxin, compared with the immunoglobulins or immunoglobulin fragments of the prior art.

Figure 2:
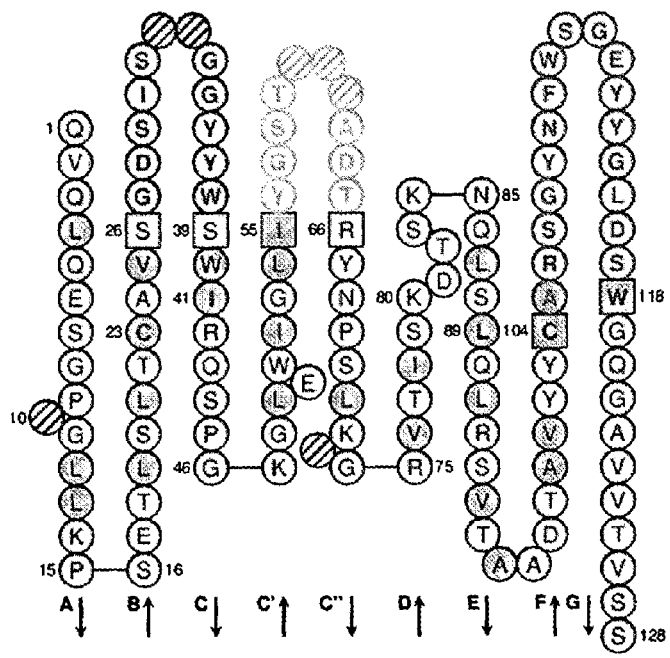
Figure 2:
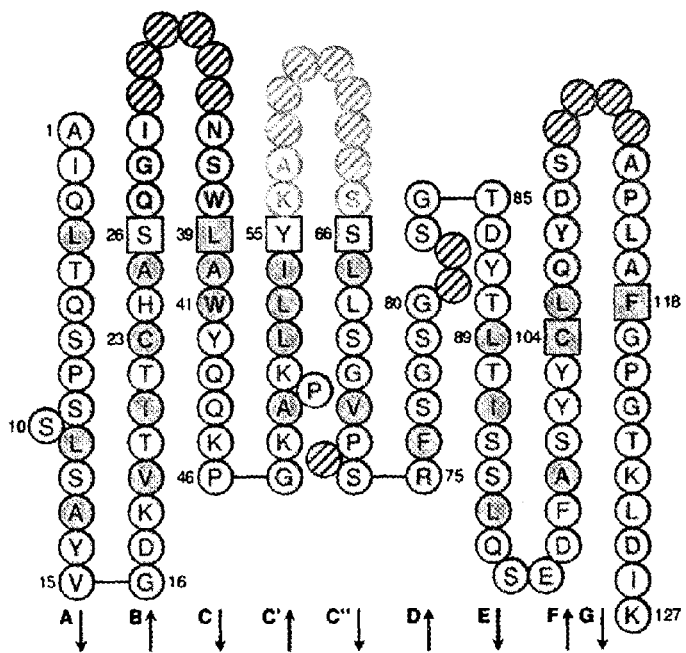

The presence of a leucine residue in position 51 of SEQ ID No.: 1 corresponds to the leucine in position 54 in FIG. 2A.

The presence of a glycine residue in position 67 of SEQ ID No.: 1 corresponds to the glycine in position 74 in FIG. 2A.

The presence of a leucine residue in position 55 of SEQ ID No.: 2 corresponds to the leucine in position 68 in FIG. 2B.

Preferably, the invention relates to a class-G immunoglobulin (IgG) directed against the anthrax toxin protective antigen (PA), or a fragment thereof, comprising:
  a heavy-chain variable region comprising the sequence
    SEQ ID No.: 1, and/or
  a light-chain variable region comprising the sequence
    SEQ ID No.: 2.

The kinetic constants for the interaction between the immunoglobulin of the invention and the PA antigen, including the affinity constant ($K_D$), can be determined by the conventional techniques known to those skilled in the art, in particular according to the method described in example 4.

In one particular embodiment, the invention relates to an immunoglobulin or a fragment thereof as defined above, in which:
  the constant region of said heavy chain comprises, or consists of, an amino acid sequence represented by the sequence SEQ ID No.: 3, and
  the light-chain constant region comprises, or consists of, an amino acid sequence represented by the sequence SEQ ID No.: 4.

In one particular embodiment, the invention relates to an immunoglobulin as defined above, in which:
  each of the heavy chains comprises, or consists of, an amino acid sequence represented by SEQ ID No.: 5, and
  each of the light chains comprises, or consists of, an amino acid sequence represented by SEQ ID No.: 6.

Such an immunoglobulin is called 35PA83 "6.20" in the present application.

In one embodiment, the invention relates to an immunoglobulin or a fragment thereof as defined above, in which said heavy chain and/or said light chain is bonded to a signal peptide.

It should be noted that the signal peptide used in the invention may be different than the signal peptide naturally associated with a given protein. The use of a signal peptide makes it possible to increase the level of secretion of a polypeptide of interest.

Such a signal peptide can, for example, be optimized so as to increase the level of secretion of the immunoglobulin of the invention.

Thus, a signal peptide known to those skilled in the art can be used, for instance a signal peptide as described in document WO 2011/114063.

In one particular embodiment, the signal peptide consists of the following amino acid sequence: MRWSWIFLLLL-SITSANA (SEQ ID No.: 19).

In one advantageous embodiment, the invention relates to an immunoglobulin as defined above, in which:
- each of the heavy chains comprises, or consists of, an amino acid sequence represented by SEQ ID No.: 7, and
- each of the light chains comprises, or consists of, an amino acid sequence represented by SEQ ID No.: 8.

The reference sequences of the heavy and light chains, or chain fragments, of the immunoglobulin of the invention are presented in table 1 below.

TABLE 1

The signal peptide is underlined. The variable region is indicated in italics.

| | |
|---|---|
| SEQ ID No.: 1 Heavy-chain variable region | *QVQLQESGPGLLKPSETLSLTCAVSGDSISGGYYWSW IRQSPGKGLEWIGLIYGSTADTRYNPSLKGRVTISKD TSKNQLSLQLRSVTAADTAVYYCARSGYNFWSGEYYG LDSWGQGAVVTVSS* |
| SEQ ID No.: 2 Light-chain variable region | *AIQLTQSPSSLSAYVGDKVTITCHASQGINSWLAWYQ QKPGKAPKLLIYKASSLLSGVPSRFSGSGSGTDYTLT ISSLQSEDFASYYCLQYDSAPLAFGPGTKLDIK* |
| SEQ ID No.: 3 Heavy-chain constant region | ASTKGPSVFPLAPSSKSTSGGTAALGCLVKDYFPEPV TVSWNSGALTSGVHTFPAVLQSSGLYSLSSVVTVPSS SLGTQTYICNVNHKPSNTKVDKKVEPKSCDKTHTCPP CPAPELLGGPSVFLFPPKPKDTLMISRTPEVTCVVVD VSHEDPEVKFNWYVDGVEVHNAKTKPREEQYNSTYRV VSVLTVLHQDWLNGKEYKCKVSNKALPAPIEKTISKA KGQPREPQVYTLPPSRDELTKNQVSLTCLVKGFYPSD IAVEWESNGQPENNYKTTPPVLDSDGSFFLYSKLTVD KSRWQQGNVFSCSVMHEALHNHYTQKSLSLSPGK |
| SEQ ID No.: 4 Light-chain constant region | RTVAAPSVFIFPPSDEQLKSGTASVVCLLNNFYPREA KVQWKVDNALQSGNSQESVTEQDSKDSTYSLSSTLTL SKADYEKHKVYACEVTHQGLSSPVTKSFNRGEC |
| SEQ ID No.: 5 Complete heavy chain without signal peptide | *QVQLQESGPGLLKPSETLSLTCAVSGDSISGGYYWSW IRQSPGKGLEWIGLIYGSTADTRYNPSLKGRVTISKD TSKNQLSLQLRSVTAADTAVYYCARSGYNFWSGEYYG LDSWGQGAVVTVSS*ASTKGPSVFPLAPSSKSTSGGTA ALGCLVKDYFPEPVTVSWNSGALTSGVHTFPAVLQSS GLYSLSSVVTVPSSSLGTQTYICNVNHKPSNTKVDKK VEPKSCDKTHTCPPCPAPELLGGPSVFLFPPKPKDTL MISRTPEVTCVVVDVSHEDPEVKFNWYVDGVEVHNAK TKPREEQYNSTYRVVSVLTVLHQDWLNGKEYKCKVSN KALPAPIEKTISKAKGQPREPQVYTLPPSRDELTKNQ VSLTCLVKGFYPSDIAVEWESNGQPENNYKTTPPVLD SDGSFFLYSKLTVDKSRWQQGNVFSCSVMHEALHNHY TQKSLSLSPGK |

TABLE 1-continued

The signal peptide is underlined. The variable region is indicated in italics.

| | |
|---|---|
| SEQ ID No.: 6 Complete light chain without signal peptide | *AIQLTQSPSSLSAYVGDKVTITCHASQGINSWLAWYQ QKPGKAPKLLIYKASSLLSGVPSRFSGSGSGTDYTLT ISSLQSEDFASYYCLQYDSAPLAFGPGTKLDIK*RTVA APSVFIFPPSDEQLKSGTASVVCLLNNFYPREAKVQW KVDNALQSGNSQESVTEQDSKDSTYSLSSTLTLSKAD YEKHKVYACEVTHQGLSSPVTKSFNRGEC |
| SEQ ID No.: 7 Heavy chain with signal peptide | <u>MRWSWIFLLLLSITSANA</u>*QVQLQESGPGLLKPSETLS LTCAVSGDSISGGYYWSWIRQSPGKGLEWIGLIYGST ADTRYNPSLKGRVTISKDTSKNQLSLQLRSVTAADTA VYYCARSGYNFWSGEYYGLDSWGQGAVVTVSS*ASTKG PSVFPLAPSSKSTSGGTAALGCLVKDYFPEPVTVSWN SGALTSGVHTFPAVLQSSGLYSLSSVVTVPSSSLGTQ TYICNVNHKPSNTKVDKKVEPKSCDKTHTCPPCPAPE LLGGPSVFLFPPKPKDILMISRTPEVTCVVVDVSHED PEVKFNWYVDGVEVHNAKTKPREEQYNSTYRVVSVLT VLHQDWLNGKEYKCKVSNKALPAPIEKTISKAKGQPR EPQVYTLPPSRDELTKNQVSLTCLVKGFYPSDIAVEW ESNGQPENNYKTTPPVLDSDGSFFLYSKLTVDKSRWQ QGNVFSCSVMHEALHNHYTQKSLSLSPGK |
| SEQ ID No.: 8 Light chain with signal peptide | <u>MRWSWIFLLLLSITSANA</u>*AIQLTQSPSSLSAYVGDKV TITCHASQG1NSWLAWYQQKPGKAPKLLIYKASSLLS GVPSRFSGSGSGTDYTLTISSLQSEDFASYYCLQYDS APLAFGPGTKLDIKRT*VAAPSVFIFPPSDEQLKSGTA SVVCLLNNFYPREAKVQWKVDNALQSGNSQESVTEQD SKDSTYSLSSTLTLSKADYEKHKVYACEVTHQGLSSP VTKSFNRGEC |

The constant regions of each of the light chains and of each of the heavy chains of the antibody that are used in the invention may be human constant regions.

This embodiment of the invention makes it possible to decrease the immunogenicity of the antibody in humans and by the same token to improve its efficacy when it is administered therapeutically to humans. In addition, the human constant regions make it possible to provide a longer half-life in humans, via the interaction with the FcRn receptors.

Preferably, the constant regions of each of the light chains of the immunoglobulin of the invention are of κ type.

Alternatively, the constant region of each of the light chains of the immunoglobulin of the invention is of λ type.

In one particular embodiment, and in particular when the constant regions of each of the light chains and of each of the heavy chains of the immunoglobulin of the invention are human regions, the constant region of each of the heavy chains of the antibody may be of γ1 type, of γ2 type, of γ3 type, or else of γ4 type.

In one preferred embodiment, the invention relates to an immunoglobulin or a fragment thereof as defined above, in which the constant region of each of the heavy chains is of γ1 type.

In one embodiment, the invention relates to an immunoglobulin or a fragment thereof as defined above, which has, on its Asn297 glycosylation site, N-glycans of which the degree of fucosylation is less than 65%, preferably less than 50%, more preferably less than 40%.

In one embodiment, the present invention relates to a class-G immunoglobulin (IgG) directed against the anthrax toxin protective antigen (PA), or a fragment thereof, comprising:

a heavy-chain variable region comprising an amino acid sequence having at least 90% amino acid identity with the sequence SEQ ID No.: 1, preferably comprising the sequence SEQ ID No.: 2, it being understood that it comprises the amino acids leucine in position 51 and glycine in position 67, and a light-chain variable region comprising an amino acid sequence having at least 90% amino acid identity with the sequence SEQ ID No.: 2, preferably comprising the sequence SEQ ID No.: 2, it being understood that it comprises leucine in position 55, said immunoglobulin or a fragment thereof having an affinity constant ($K_D$) with respect to said anthrax toxin protective antigen of less than $2\times10^{-9}$ M, preferably less than or equal to $3.3\times10^{-11}$ M, said immunoglobulin having, on its Asn297 glycosylation site, N-glycans of which the degree of fucosylation is less than 65%, preferably less than 50%, more preferably less than 40%.

In one particular embodiment, the invention relates to an immunoglobulin or a fragment thereof as defined above, in which:

the constant region of said heavy chain comprises, or consists of, an amino acid sequence represented by the sequence SEQ ID No.: 3, and the light-chain constant region comprises, or consists of, an amino acid sequence represented by the sequence SEQ ID No.: 4, said immunoglobulin or a fragment thereof having an affinity constant ($K_D$) with respect to said anthrax toxin protective antigen of less than $2\times10^{-9}$ M, preferably less than or equal to $3.3\times10^{-11}$ M, said immunoglobulin having, on its Asn297 glycosylation site, N-glycans of which the degree of fucosylation is less than 65%, preferably less than 50%, more preferably less than 40%.

In one particular embodiment, the invention relates to an immunoglobulin as defined above, in which:

each of the heavy chains comprises, or consists of, an amino acid sequence represented by SEQ ID No.: 5, and each of the light chains comprises, or consists of, an amino acid sequence represented by SEQ ID No.: 6, said immunoglobulin having an affinity constant ($K_D$) with respect to said anthrax toxin protective antigen of less than $2\times10^{-9}$ M, preferably less than or equal to $3.3\times10^{-11}$ M, said immunoglobulin having, on its Asn297 glycosylation site, N-glycans of which the degree of fucosylation is less than 65%, preferably less than 50%, more preferably less than 40%.

In one particular embodiment, the invention relates to an immunoglobulin as defined above, in which:

each of the heavy chains comprises, or consists of, an amino acid sequence represented by SEQ ID No.: 7, and each of the light chains comprises, or consists of, an amino acid sequence represented by SEQ ID No.: 8, said immunoglobulin having an affinity constant ($K_D$) with respect to said anthrax toxin protective antigen of less than $2\times10^{-9}$ M, preferably less than or equal to $3.3\times10^{-11}$ M, said immunoglobulin having, on its Asn297 glycosylation site, N-glycans of which the degree of fucosylation is less than 65%, preferably less than 50%, more preferably less than 40%.

The immunoglobulins of the invention therefore differ in particular from the anti-anthrax toxin immunoglobulins already known by virtue of their low degree of fucosylation.

Furthermore, the immunoglobulins of the invention also have a particular N-glycosylation profile.

In one particular embodiment, the invention relates to an immunoglobulin or a fragment thereof as defined above, having, on its Asn297 glycosylation site, a glycan structure of biantennary type, with short chains and a low degree of sialylation, having non-intercalated end mannoses and/or end N-acetylglucosamines.

The glycosylated forms that can be envisioned for the immunoglobulins according to the invention are presented in table 2 below.

TABLE 2

| Symbol | Glycosylated form |
|---|---|
| G0 | Biantennary complex with agalactosylated structure |
| G1 | Biantennary complex with a structure comprising a single galactose |
| G0F | Biantennary complex with agalactosylated structure (G0), in which the pentasaccharide nucleus is substituted with a fucose |
| G1F | Biantennary complex with a structure comprising a single galactose (G1), in which the pentasaccharide nucleus is substituted with a fucose |

In one embodiment, the invention relates to an immunoglobulin or a fragment thereof as defined above, having a content of greater than 60% for the G0+G1+G0F+G1F forms, the content of the G0F+G1F forms being less than 50%.

In one embodiment, the invention relates to an immunoglobulin or a fragment thereof as defined above, having a content of greater than 60% for the G0+G1+G0F+G1F forms, the fucose content being less than 65%.

In one embodiment, the invention relates to an immunoglobulin or a fragment thereof as defined above, having a content of less than 40% for the G0F+G1F forms.

Another aspect of the invention is a polynucleotide encoding the immunoglobulin of the invention or a fragment thereof.

Thus, another aspect of the invention relates to a polynucleotide comprising at least one nucleotide sequence encoding the heavy chain or the light chain of an immunoglobulin or a fragment thereof as defined above.

In one particular embodiment, the invention relates to a polynucleotide comprising at least one nucleotide sequence chosen from SEQ ID Nos: 9, 10, 11, 12, 13, 14, 15, 16, 17 and 18.

TABLE 3

The coding sequences are indicated in bold. The sequences encoding the signal peptide are in bold, italics, and are underlined. The Kozak sequences are underlined. The stop codons are in italics and underlined.

| | |
|---|---|
| SEQ ID No.: 9<br>Nucleotide sequence encoding the variable part of the heavy chain | caggtgcagctgcaggaatctggccctggcctgctgaagcccagcgagacactgtctc<br>tgacctgcgccgtgtccggcgactctatcagcggcggctactactggtcttggatcag<br>gcagagccccggcaagggcctggaatggatcggcctgatctacggcagcaccgccgac<br>accagatacaaccccagcctgaagggcagagtgaccatcagcaaggacaccagcaaga<br>accagctgtctctgcagctgagaagcgtgaccgctgccgacaccgccgtgtactactg<br>tgccagaagcggctacaacttttggagcggcgagtactacggcctggactcttgggga<br>cagggcgctgtcgtgacagtgtccagc |
| SEQ ID No.: 10<br>Nucleotide sequence encoding the variable part of the light chain | gccatccagctgacccagagccctagctctctgagcgcctacgtgggcgacaaagtga<br>ccatcacctgtcacgccagccagggcatcaacagctggctggcctggtatcagcagaa<br>gcccggcaaggcccccaagctgctgatctacaaggccagcagcctgctgagcggcgtg<br>cccagcagattcagcggctctggctctggcaccgactacaccctgaccatcagctccc<br>tgcagagcgaggacttcgccagctactactgcctgcagtacgacagcgcccctctggc<br>cttcggccctggaacaaagctggacatcaag |
| SEQ ID No.: 11<br>Nucleotide sequence encoding the constant part of the heavy chain | gcctctaccaagggcccaagcgtgttccctctggcccctagcagcaagtctacctctg<br>gcggaacagccgccctgggctgcctcgtgaaggactactttcccgagcccgtgaccgt<br>gtcctggaactctggcgctctgacaagcggcgtgcacaccttccctgccgtgctgcag<br>tctagcggcctgtacagcctgagcagcgtcgtgactgtgccctctagctctctgggca<br>cccagacctacatctgcaacgtgaaccacaagcccagcaacaccaaggtggacaagaa<br>ggtggaacccaagagctgcgacaagacccacacctgtcctccctgtcctgcccctgaa<br>ctgctgggcggaccttccgtgttcctgttccccccaaagcctaaggacaccctgatga<br>tcagcaggaccccgaagtgacctgcgtggtggtggatgtgtcccacgaggaccctga<br>agtgaagttcaattggtacgtggacggcgtggaagtgcacaacgccaagaccaagcct<br>agagaggaacagtacaacagcacctacagggtggtgtctgtgctgacagtgctgcacc<br>aggactggctgaacggcaaagagtacaagtgcaaggtgtccaacaaggccctgccagc<br>ccccatcgaaagaccatctccaaggccaagggacagcctcgcgagccccaggtgtac<br>acactgcctcccagcagggacgagctgacaaagaatcaggtgtccctgacctgtctcg<br>tgaaaggcttctaccccagcgacattgccgtggaatgggagagcaacggccagcccga<br>gaacaactacaagaccaccccccctgtgctggacagcgacggctcattcttcctgtac<br>tccaagctgaccgtggacaagtccaggtggcagcagggcaacgtgttcagctgctccg<br>tgatgcacgaggccctgcacaaccactacacccagaagtccctgagcctgagccctgg<br>caag |
| SEQ ID No.: 12<br>Nucleotide sequence encoding the constant part of the light chain | aggaccgtggccgcaccaagtgtctttatcttcccacccagcgacgagcagctgaagt<br>ccggcacagcttccgtcgtgtgcctgctgaacaacttctacccaggggaagccaaggt<br>gcagtggaaggtggacaacgcccctgcagtccggcaactcccaggaaagcgtgaccgag<br>caggacagcaaggactccacctacagcctgagcagcaccctgacactgagcaaggccg<br>actacgagaaacataaggtgtacgcctgcgaagtgacccaccagggcctgtctagccc<br>cgtgaccaagagcttcaacaggggcgagtgc |
| SEQ ID No.: 13<br>Nucleotide sequence encoding the heavy chain | caggtgcagctgcaggaatctggccctggcctgctgaagcccagcgagacactgtctc<br>tgacctgcgccgtgtccggcgactctatcagcggcggctactactggtcttggatcag<br>gcagagccccggcaagggcctggaatggatcggcctgatctacggcagcaccgccgac<br>accagatacaaccccagcctgaagggcagagtgaccatcagcaaggacaccagcaaga<br>accagctgtctctgcagctgagaagcgtgaccgctgccgacaccgccgtgtactactg<br>tgccagaagcggctacaacttttggagcggcgagtactacggcctggactcttgggga<br>cagggcgctgtcgtgacagtgtccagcgcctctaccaagggcccaagcgtgttccctc<br>tggcccctagcagcaagtctacctctggcggaacagccgccctgggctgcctcgtgaa<br>ggactactttcccgagcccgtgaccgtgtcctggaactctggcgctctgacaagcggc<br>gtgcacaccttccctgccgtgctgcagtctagcggcctgtacagcctgagcagcgtcg<br>tgactgtgccctctagctctctgggcacccagacctacatctgcaacgtgaaccacaa<br>gcccagcaacaccaaggtggacaagaaggtggaacccaagagctgcgacaagacccac<br>acctgtcctccctgtcctgcccctgaactgctgggcggaccttccgtgttcctgttcc<br>ccccaaagcctaaggacaccctgatgatcagcaggaccccgaagtgacctgcgtggt<br>ggtggatgtgtcccacgaggaccctgaagtgaagttcaattggtacgtggacggcgtg<br>gaagtgcacaacgccaagaccaagcctagagaggaacagtacaacagcacctacaggg<br>tggtgtctgtgctgacagtgctgcaccaggactggctgaacggcaaagagtacaagtg<br>caaggtgtccaacaaggccctgccagcccccatcgaaagaccatctccaaggccaag<br>ggacagcctcgcgagccccaggtgtacacactgcctcccagcagggacgagctgacaa<br>agaatcaggtgtccctgacctgtctcgtgaaaggcttctaccccagcgacattgccgt<br>ggaatgggagagcaacggccagcccgagaacaactacaagaccaccccccctgtgctg<br>gacagcgacggctcattcttcctgtactccaagctgaccgtggacaagtccaggtggc<br>agcagggcaacgtgttcagctgctccgtgatgcacgaggccctgcacaaccactacac<br>ccagaagtccctgagcctgagccctggcaag |

TABLE 3-continued

The coding sequences are indicated in bold. The sequences encoding the signal peptide are in bold, italics, and are underlined. The Kozak sequences are underlined. The stop codons are in italics and underlined.

| | |
|---|---|
| SEQ ID No.: 14<br>Nucleotide sequence encoding the light chain | gccatccagctgacccagagccctagctctctgagcgcctacgtgggcgacaaagtga<br>ccatcacctgtcacgccagccagggcatcaacagctggctggcctggtatcagcagaa<br>gccggcaaggcccccaagctgctgatctacaaggccagcagcctgctgagcggcgtg<br>cccagcagattcagcggctctggctctggcaccgactacaccctgaccatcagctccc<br>tgcagagcgaggacttcgccagctactactgcctgcagtacgacagcgccctctggc<br>cttcggccctggaacaaagctggacatcaagaggaccgtggccgcaccaagtgtcttt<br>atcttcccacccagcgacgagcagctgaagtccggcacagcttccgtcgtgtgcctgc<br>tgaacaacttctaccctagggaagccaaggtgcagtggaaggtggacaacgccctgca<br>gtccggcaactcccaggaaagcgtgaccgagcaggacagcaaggactccacctacagc<br>ctgagcagcaccctgacactgagcaaggccgactacgagaaacataaggtgtacgcct<br>gcgaagtgacccaccagggcctgtctagcccgtgaccaagagcttcaacaggggcga<br>gtgc |
| SEQ ID No.: 15<br>Nucleotide sequence encoding the heavy chain comprising an N-terminal signal peptide | *<u>atgcgatggtcctggatcttcctgctgctgctgagcatcaccagcgccaacgctc</u>*<br>aggtgcagctgcaggaatctggccctggcctgctgaagcccagcgagacactgtctct<br>gacctgcgccgtgtccggcgactctatcagcggcggctactactggtcttggatcagg<br>cagagccccggcaagggcctggaatggatcggcctgatctacggcagcagcgccgaca<br>ccagatacaaccccagcctgaagggcagagtgaccatcagcaaggacaccagcaagaa<br>ccagctgtctctgcagctgagaagcgtgaccgctgccgacaccgccgtgtactactgt<br>gccagaagcggctacaacttaggagcggcgagtactacggcctggactcaggggacag<br>ggcgctgtcgtgacagtgtccagcgcctctaccaagggcccaagcgtgttccctctgg<br>cccctagcagcaagtctacctctggcggaacagccgccctgggctgcctcgtgaagga<br>ctactttcccgagcccgtgaccgtgtcctggaactctggcgctctgacaagcggcgtg<br>cacaccttccctgccgtgctgcagtctagcggcctgtacagcctgagcagcgtcgtga<br>ctgtgccctctagctctctgggcacccagacctacatctgcaacgtgaaccacaagcc<br>cagcaacaccaaggtggacaagaaggtggaacccaagagctgcgacaagacccacacc<br>tgtcctccctgtcctgcccctgaactgctgggcggaccttccgtgttcctgttccccc<br>caaagcctaaggacaccctgatgatcagcaggaccccgaagtgacctgcgtggtggt<br>ggatgtgtcccacgaggaccctgaagtgaagttcaattggtacgtggacggcgtggaa<br>gtgcacaacgccaagaccaagcctagagaggaacagtacaacagcacctacagggtgg<br>tgtctgtgctgacagtgctgcaccaggactggctgaacggcaaagagtacaagtgcaa<br>ggtgtccaacaaggccctgccagcccccatcgaaaagaccatctccaaggccaaggga<br>cagcctcgcgagcccaggtgtacacactgcctcccagcagggacgagctgacaaaga<br>tcaggtgtccctgacctgtctcgtgaaaggcttctaccccagcgacattgccgtgga<br>atgggagagcaacggccagcccgagaacaactacaagaccacccccctgtgctggac<br>agcgacggctcattcttcctgtactccaagctgaccgtggacaagtccaggtggcagc<br>agggcaacgtgacagctgctccgtgatgcacgaggccctgcacaaccactacacccag<br>aagtccctgagcctgagccctggcaag |
| SEQ ID No.: 16<br>Nucleotide sequence encoding the light chain comprising an N-terminal signal peptide | *<u>atgcgatggtcctggatcttcctgctgctgctgagcatcaccagcgccaacgccg</u>*<br>ccatccagctgacccagagccctagctctctgagcgcctacgtgggcgacaaagtgac<br>catcacctgtcacgccagccagggcatcaacagctggctggcctggtatcagcagaag<br>cccggcaaggcccccaagctgctgatctacaaggccagcagcctgctgagcggcgtgc<br>ccagcagattcagcggctctggctctggcaccgactacaccctgaccatcagctcct<br>gcagagcgaggacttcgccagctactactgcctgcagtacgacagcgccctctggcc<br>acggccctggaacaaagctggacatcaagaggaccgtggccgcaccaagtgtctttat<br>cttcccacccagcgacgagcagctgaagtccggcacagcttccgtcgtgtgcctgctg<br>aacaacttctaccctagggaagccaaggtgcagtggaaggtggacaacgccctgcagt<br>ccggcaactcccaggaaagcgtgaccgagcaggacagcaaggactccacctacagcct<br>gagcagcaccctgacactgagcaaggccgactacgagaaacataaggtgtacgcctgc<br>gaagtgacccaccagggcctgtctagcccgtgaccaagagcttcaacaggggcgagt<br>gc |
| SEQ ID No.: 17<br>Nucleotide sequence encoding the heavy chain as synthesized | gctagcgccgccacc*<u>atgcgatggtcctggatcttcctgctgctgctgagcatcac</u>*<br>*<u>cagcgccaacgct</u>*caggtgcagctgcaggaatctggccctggcctgctgaagcccag<br>cgagacactgtctctgacctgcgccgtgtccggcgactctatcagcggcggctactac<br>tggtcttggatcaggcagagccccggcaagggcctggaatggatcggcctgatctacg<br>gcagcagcgccgacaccagatacaaccccagcctgaagggcagagtgaccatcagcaa<br>ggacaccagcaagaaccagctgtctctgcagctgagaagcgtgaccgctgccgacacc<br>gccgtgtactactgtgccagaagcggctacaacttttggagcggcgagtactacggcc<br>tggactcttggggacagggcgctgtcgtgacagtgtccagcgcctctaccaagggccc<br>aagcgtgttccctctggcccctagcagcaagtctacctctggcggaacagccgccctg<br>ggctgcctcgtgaaggactactttcccgagcccgtgaccgtgtcctggaactctggcg<br>ctctgacaagcggcgtgcacaccttccctgccgtgctgcagtctagcggcctgtaca<br>gcctgagcagcgtcgtgactgtgccctctagctctctgggcacccagacctacatctg<br>caacgtgaaccacaagcccagcaacaccaaggtggacaagaaggtggaacccaagagc<br>tgcgacaagacccacacctgtcctccctgtcctgcccctgaactgctgggcggaccttc<br>cgtgttcctgttccccccaaagcctaaggacaccctgatgatcagcaggaccccga<br>agtgacctgcgtggtggtggatgtgtcccacgaggaccctgaagtgaagttcaattgg<br>tacgtggacggcgtggaagtgcacaacgccaagaccaagcctagagaggaacagtaca<br>acagcacctacagggtggtgtctgtgctgacagtgctgcaccaggactggctgaacgg<br>caaagagtacaagtgcaaggtgtccaacaaggccctgccagcccccatcgaaaagacc<br>atctccaaggccaagggacagcctcgcgagcccaggtgtacacactgcctcccagca<br>gggacgagctgacaaagaatcaggtgtccctgacctgtctcgtgaaaggcttctaccc<br>cagcgacattgccgtggaatgggagagcaacggccagcccgagaacaactacaagacc<br>accccccctgtgctggacagcgacggctcattcttcctgtactccaagctgaccgtgg |

TABLE 3-continued

The coding sequences are indicated in bold. The sequences encoding the signal peptide are in bold, italics, and are underlined. The Kozak sequences are underlined. The stop codons are in italics and underlined.

| | |
|---|---|
| | acaagtccaggtggcagcagggcaacgtgttcagctgctccgtgatgcacgaggccct gcacaaccactacacccagaagtccctgagcctgagccctggcaag*tgatag*ggcgcg cc |
| SEQ ID No.: 18<br>Nucleotide sequence<br>encoding the light<br>chain as synthesized | actagt<u>gccacc</u>**<u>*atgcgatggtcctggatcttcctgctgctgctgagcatcac*</u>** **<u>*cagcgccaacgcc*</u>**gccatccagctgacccagagccctagctctctgagcgcctacgt gggcgacaaagtgaccatcacctgtcacgccagccagggcatcaacagctggctggcc tggtatcagcagaagcccggcaaggcccccaagctgctgatctacaaggccagcagcc tgctgagcggcgtgcccagcagattcagcggctctggctctggcaccgactacaccct gaccatcagctccctgcagagcgaggacttcgccagctactactgcctgcagtacgac agcgccctctggccttcggccctggaacaaagctggacatcaagaggaccgtggccg caccaagtgtctttatcttcccacccagcgacgagcagctgaagtccggcacagcttc cgtcgtgtgcctgctgaacaacttctaccctagggaagccaaggtgcagtggaaggtg gacaacgccctgcagtccggcaactcccaggaaagcgtgaccgagcaggacagcaagg actccacctacagcctgagcagcaccctgacactgagcaaggccgactacgagaaaca taaggtgtacgcctgcgaagtgacccaccagggcctgtctagccccgtgaccaagagc ttcaacaggggcgagtgc<u>*tagtga*</u>actctaga |

Such polynucleotides can be inserted into a recombinant vector for cloning or for expression of the immunoglobulins of the invention.

Another aspect of the invention is therefore a vector comprising a polynucleotide encoding the immunoglobulin of the invention or a fragment thereof.

The term "vector" refers to a nucleic acid molecule into which a sequence of interest can be inserted by digestion with a restriction endonuclease, then ligation, for transport between various genetic environments or for expression in a host cell. The vectors are for example plasmids, cosmids, yeast artificial chromosomes (YACs), bacterial artificial chromosomes (BACs) and bacteriophage P1-derived artificial chromosomes (PACs), and virus-derived vectors.

A cloning vector is a vector capable of replicating in a host cell and which is furthermore characterized by the presence of one or more restriction sites.

An expression vector is a vector into which the DNA sequence of interest can be inserted by digestion with a restriction endonuclease and ligation in such a way that it can be replicated and/or transcribed into RNA.

The vectors may also contain one or more markers for selection or identification of the cells having been transformed or transfected with the vector.

The present invention includes all recombinant vectors containing coding sequences for gene transformation, transfection or therapy, which may be eukaryotic or prokaryotic. Such vectors may be prepared according to conventional molecular biology techniques and will also comprise an appropriate promoter, optionally a signal sequence for export or secretion, and regulatory sequences required for transcription of the nucleotide sequence.

The vector of the invention may comprise the sequences encoding the heavy chain and/or the light chain of the immunoglobulin of the invention.

One embodiment of the invention thus relates to a vector comprising at least one polynucleotide as defined above, comprising at least one nucleotide sequence encoding the heavy chain or the light chain of an immunoglobulin as defined above.

Another embodiment of the invention relates to a vector comprising at least one polynucleotide as defined above, comprising at least one nucleotide sequence encoding the heavy chain and one sequence encoding the light chain of an immunoglobulin as defined above.

One of the vectors that is appropriate in the context of the invention is a recombinant nucleic acid molecule suitable for receiving and expressing a first polynucleotide and a second polynucleotide, so as to allow the expression of a heterodimeric antibody such as a full-length antibody or F(ab')2 or Fab fragments according to the invention.

Such a vector provides a system for independently cloning the two polynucleotides in two separate cassettes present in the vector, so as to form two separate cistrons for the expression of a first and of a second polypeptide of the heterodimeric antibody. Such an expression vector is called a bicistronic vector.

In one particular embodiment, the vector is a nucleic acid molecule into which a polynucleotide encoding the variable region of each of the light chains of the immunoglobulin, and a polynucleotide encoding the constant region of each of the light chains of the immunoglobulin, have been inserted, in order to introduce them into and maintain them in a host cell. Such a vector allows the expression of these polynucleotides in the host cell since it has sequences that are essential (promoter, polyadenylation sequence, selectable gene) to this expression. Such vectors are well known to those skilled in the art, and may be an adenovirus, a retrovirus, a plasmid or a bacteriophage, this list not being limiting.

It is moreover possible to introduce, into such a vector, transcription units, i.e. polynucleotides containing regulatory elements required for the transcription of a nucleic acid of interest into RNA.

Transcription units known to those skilled in the art can be used, for instance those described in document WO 2013/061010.

The immunoglobulin-producing host cell is an important characteristic since it confers on the immunoglobulin some of its specific properties. Indeed, the means of expressing the immunoglobulins is responsible for post-translational modifications, in particular glycosylation modifications, which can vary from one cell line to the other, and thus confer different functional properties on immunoglobulins which nevertheless have identical primary structures.

Another aspect of the invention thus relates to a host cell comprising a vector as defined above.

Such a host cell may be a prokaryotic or eukaryotic cell. The immunoglobulins of the present invention may in particular be produced in eukaryotic cells, such as YB2/0 or CHO cells, or human or murine hybridomas, and also in plant cells and transgenic animals.

In one particular embodiment, the invention relates to a host cell as defined above, characterized in that it is a cell chosen from: SP2/0, YB2/0, IR983F, the Namalwa human myeloma, PERC6, the CHO lines, in particular CHO-K-1, CHO-Led O, CHO-Led, CHO-Lec13, CHO Pro-5, CHO dhfr–, Wil-2, Jurkat, Vero, Molt-4, COS-7, 293-HEK, BHK, K6H6, NSO, SP2/0-Ag 14 and P3X63Ag8.653.

In another preferred embodiment, the immunoglobulin is produced in the YB2/0 rat hybridoma (cell YB2/3HL. P2. G11.16Ag.20, deposited with the American Type Culture Collection under number ATCC No. CRL-1662).

Preferably, the stable cell line expressing an immunoglobulin according to the invention, and more particularly chosen from the group described above, has integrated the vector(s) for expression of the heavy chain and of the light chain as described above.

Other methods are known to those skilled in the art for producing immunoglobulins with a low degree of fucosylation, and can be used for preparing the immunoglobulins of the invention.

Non-exhaustively, they may be, for example, methods for preparing antibodies in cells cultured in the presence of kifunensine, as is described for example in document U.S. Pat. No. 7,700,321.

Fucose analogs may also be introduced into the culture medium of antibody-producing cells, as described in document US 2009/0317869.

Another means for producing the antibodies may be the use, for example, of cells for which the GDP-fucose production pathway is inhibited, for example by inhibition of at least one of the enzymes of the fucose production cycle, as described for example in document US 2010/291628 or US 2009/0228994, document EP 1 500 698, document EP 1 792 987 or else document U.S. Pat. No. 7,846,725, this list not being limiting.

It is also possible to use interfering RNAs (iRNAs) which inhibit 1,6-fucosyltransferase, as described in document U.S. Pat. No. 7,393,683 or document WO 2006/133148.

They may also be methods for preparing antibodies in transgenic animals, as is described in document WO 2007/48077. They may also be methods for preparing antibodies in yeasts, as is described for example in document WO 02/00879.

In the case where the Fc region of the antibody has 100% non-fucosylated oligosaccharides, i.e. when the Fc region of the antibody is totally devoid of fucose, it is possible to use preparation methods known to those skilled in the art, for instance those described in documents EP 1 176 195, U.S. Pat. No. 7,214,775, U.S. Pat. No. 6,994,292, U.S. Pat. No. 7,425,449, US 2010/223686, WO 2007/099988 or EP 1 705 251, this list not being limiting. They may for example involve a method using a host cell expressing at least one nucleic acid encoding the antibody of the invention, and in which the glycosylation is modified by deletion of the gene encoding α-1,6-fucosyltransferase or by addition of a mutation of this gene in order to eliminate the α-1,6-fucosyltransferase activity, and in this respect expressing an antibody devoid of fucose. They may also involve a method comprising the mutation of the amino acids of the Fc part.

In another aspect, the invention relates to a composition, in particular a pharmaceutical composition, comprising at least one immunoglobulin, preferably human immunoglobulin, or a fragment thereof as defined above.

Such a pharmaceutical composition preferably comprises a pharmaceutically acceptable carrier.

For the purposes of the invention, such a carrier corresponds to a non-toxic material which does not interfere with the efficacy of the biological activity of the active ingredients of the composition.

The term "pharmaceutically acceptable" refers to a non-toxic material which is compatible with a biological system such as a cell, a cell culture, a tissue or an organism. The characteristics of the carrier will depend on the mode of administration.

In another aspect, the invention relates to an immunoglobulin, preferably human immunoglobulin, or a fragment thereof as defined above, for use thereof as a medicament.

In another aspect, the invention relates to an immunoglobulin, preferably human immunoglobulin, or a fragment thereof as defined above, for use thereof in the treatment or prevention of pathological conditions associated with anthrax toxins.

The term "prevention" corresponds to the prevention of the appearance of the disease in a subject, in particular a human being, in whom the disease has not yet struck.

The term "treatment" corresponds to the inhibition of this disease, i.e. the arrest of its development, its regression, or the disappearance of the symptoms and consequences of the disease, or else the disappearance of the causes of the disease.

In another aspect, the invention relates to a method for the in vitro detection of an anthrax toxin comprising the protective antigen (PA) in a biological sample, comprising:
  bringing the sample into contact with at least one immunoglobulin or a fragment thereof as defined above, and
  detecting the binding of said immunoglobulin or a fragment thereof as an indicator of the presence of said anthrax toxin.

The biological sample may be liquid, for example saliva, urine, cerebrospinal fluid, serum or blood, or solid or semi-solid, for example tissues or fecal matter or a solid tissue as commonly used in histological diagnosis.

The immunoglobulin of the invention may be used in vitro, for example in immunological tests in which immunoglobulins are used in liquid phase or attached to a solid-phase carrier. Examples of well known carriers are glass, polystyrene, polypropylene, polyethylene, dextran, nylon, amylase, natural or modified cellulose, polyacrylamide, agarose or magnetite. Examples of immunological tests using the anti-PA immunoglobulin of the invention are radioimmunoassays, immunohistological labeling, ELISAs, western blots, immunoprecipitation assays, immunodiffusion assays, complement fixing assays, flow cytometry (FACS) analyses or else protein-chip analyses.

The immunoglobulin of the invention may be labeled. Examples of labels include enzymes, radioisotopes, fluorescent compounds, colloidal metals, chemiluminescent compounds and bioluminescent compounds.

The methods for bonding a label to an immunoglobulin are well known to those skilled in the art.

Another labeling technique consists in coupling the immunoglobulin to low-molecular-weight haptens, it being possible for these haptens to be specifically modified by means of a second reaction. Examples of haptens are biotin, which reacts with avidin, or dinitrophenol, pyridoxal or fluorescein, which can react with specific anti-hapten immunoglobulins.

In another aspect, the invention relates to a kit for detecting an anthrax toxin comprising the protective antigen (PA), said kit comprising:

a container comprising at least one anti-PA immunoglobulin or a fragment thereof of the invention and which may or may not be labeled, optionally, a container comprising buffer solutions, and optionally a container comprising means for detecting the immunoglobulin or a fragment thereof, which is labeled, such as a biotin-binding protein, for example avidin or streptavidin, bonded to a reporter molecule, such as a fluorescent or enzymatic label.

This container may also comprise means for detecting the immunoglobulin or a fragment thereof which is not labeled, i.e. essentially antibodies or antibody fragments.

In one embodiment, the invention relates to a kit for detecting an anthrax toxin comprising the protective antigen (PA) as defined above, said kit comprising:

a container comprising at least one immunoglobulin or a fragment thereof as defined above, which is labeled, and a container comprising means for detecting said immunoglobulin or a fragment thereof which is labeled.

The amount of labeled immunoglobulin administered must be sufficient to allow the detection of the binding of the immunoglobulin to the toxin. The amount of labeled immunoglobulin administered will depend on factors such as the age and sex of the subject, and also on the stage of the disease. The amount administered can vary between 0.01 mg/kg and 50 mg/kg, preferably between 0.1 mg/kg and 20 mg/kg, and more preferably between 0.1 mg/kg and 2 mg/kg.

The immunoglobulin of the invention may be bonded to a radioisotope directly, or indirectly, by means of functional groups. Functional groups commonly used are, for example, diethylenetriaminepentaacetic acid (DTPA) and ethylenediaminetetraacetic acid (EDTA). Examples of radioisotope metal ions are $^{111}In$, $^{97}Ru$, $^{67}Ga$, $^{68}Ga$, $^{72}As$, $^{89}Zr$ and $^{201}Tl$.

The immunoglobulins of the invention may also be labeled with a paramagnetic isotope for diagnosis by magnetic resonance imaging (MRI) or by electron spin resonance (ESR). Positron-emitting gamma radioisotope may also be used, such as $^{157}Gd$, $^{55}Mn$, $^{162}Dy$, $^{68}Ga$, $^{52}Cr$ and $^{56}Fe$.

The immunoglobulins or a fragment thereof of the invention may also be used in vitro or in vivo for monitoring the progress of the treatment of the disease, for example by determining the increase or decrease in the number of cells targeted by the anthrax toxins or the changes in the concentration of the PA toxin in a biological sample.

In another aspect, the present invention also relates to a method for treating a subject, preferably a human being, who may be infected with *Bacillus anthracis*, in which a therapeutically effective amount of an immunoglobulin according to the invention is administered to said subject.

The term "therapeutically effective amount" refers to the amount which is sufficient to perform the treatment when it is administered to a subject who requires such a treatment. The effective therapeutic amount depends on the subject, on the stage of the disease to be treated and on the mode of administration, and can be determined by routine operations by those skilled in the art.

The term "anthrax" refers to any disease caused directly or indirectly by an infection with *Bacillus anthracis*.

The initial symptoms of an infection by inhalation resemble those of a cold or of flu (fever, muscle pain). After several days, these symptoms progress to severe problems of respiratory distress and septic shock. Without any treatment, the inhalation of *Bacillus anthracis* spores is generally fatal. Cutaneous infection by anthrax occurs when the bacterium enters the skin at a pre-existing cutaneous breach. This infection gives rise, firstly, to a papule, which develops in two to three days into a vesicle and then into an ulcer of 1 to 3 centimeters in diameter which has a necrotic area at the center. Gastrointestinal infection by anthrax develops following the consumption of contaminated meat and is characterized by acute inflammation of the intestinal tract.

A therapeutically effective amount corresponds to an amount that is sufficient to reduce the symptoms of the disease and the progress of the infection. This amount may vary with the age and sex of the subject and the stage of the disease and will be determined by those skilled in the art. A therapeutically effective amount can vary between 0.01 mg/kg and 50 mg/kg, preferably between 0.1 mg/kg and 20 mg/kg, and more preferably between 0.1 mg/kg and 2 mg/kg, in one or more daily administrations, for one or more days, preferably in one or two administrations in total.

The mode of administration may be by injection or by gradual infusion. The injection may be intravenous, intraperitoneal, intramuscular, subcutaneous or transdermal.

The preparations for parenteral administration may include sterile aqueous or nonaqueous solutions, suspensions or emulsions. Examples of nonaqueous solvents are propylene glycol, polyethylene glycol, vegetable oils, such as olive oil, or injectable organic esters such as ethyl oleate. Aqueous carriers comprise water, alcohol/water solutions, emulsions or suspensions.

In another aspect, the invention relates to an immunoconjugate comprising an immunoglobulin or a fragment thereof as defined above, bonded to a therapeutic agent.

In one embodiment, the invention relates to an immunoconjugate comprising an immunoglobulin or a fragment thereof as defined above, directly or indirectly bonded to a therapeutic agent.

Such therapeutic agents comprise chemical agents, radionuclides, immunotherapeutic agents, cytokines, chemokines, toxins or enzyme inhibitors. Examples of toxins are the diphtheria A chain, the exotoxin A chain, the ricin A chain, the abrin A chain, the modeccin A chain, alpha-sarcin, *Aleurites fordii* proteins, dianthine proteins, *Phytolaca americana* proteins, *momordica charantia* inhibitor, curcin, crotin, *sapaonaria officinalis* inhibitor, gelonin, mitogellin, restrictocin, phenomycin, enomycin and tricothecenes. Examples of radionuclides are $^{212}Bi$, $^{131}I$, $^{131}In$, $^{90}Y$ and $^{186}Re$.

Advantageously, the immunoglobulin of the invention or a fragment thereof is combined with a prophylactic treatment with tetracycline. The immunoglobulin of the invention makes it possible to shorten the tetracycline-based prophylaxis, by safely stopping, after a risk of exposure, by means of a rapid treatment ("short treatment") with tetracycline followed by an injection of the immunoglobulin of the invention.

Advantageously, the immunoglobulin of the invention is combined with a curative treatment with ciprofloxacin.

The present invention will be understood more clearly by means of the following figures and examples.

FIGURE LEGENDS

FIG. 1

Pearl necklace diagram of the variable region of the heavy chain (A) and of the light chain (B) of the 35PA83 immunoglobulin.

The pearl necklace IMGT representation is produced in accordance with IMGT numbering. The hatched circles correspond to the missing positions of the IMGT numbering.

FIG. 2

Pearl necklace diagram of the variable region of the heavy chain (A) and of the light chain (B) of the 35PA83 "6.20" immunoglobulin.

The pearl necklace IMGT representation is produced in accordance with IMGT numbering. The hatched circles correspond to the missing positions of the IMGT numbering.

FIG. 3

HILIC-UPLC/FD profile of the N-glycans of the 35PA83 "6.20" antibody, released after treatment using peptidyl-N-glycosidase F (PNGase F).

The X-axis corresponds to the elution time in minutes. The Y-axis indicates the intensity noted for each compound identified, in emission units.

EXAMPLES

Example 1: Construction of the Vector Encoding the 35PA83 "6.20" Immunoglobulin

*Escherichia coli* Strains

The following *E. coli* strains were used:

XL1 (Stratagene, La jolla, CA): recA1, endA1, gyrA96 thi-1 hsdR17 sup E44 relA1 lac [F'proAB laclqZΔM15 Tn10(Tetr)].

SURE (Stratagene): e14(McrA) Δ(mcrCB-hsdSMR-mrr) 171 endA1 supE44 thi-1 gyrA96 relA1 lac recB recJ sbcC umuC::Tn5 (Kanr) uvrC [F'proAB laclqZΔM15 Tn10 (Tetr)].

HB2151 (Carte et al., 1985), used for the expression of soluble Fabs.

TOP 10 (Invitrogen): used for constructing the eukaryotic expression vector.

Toxins

The anthrax toxins (PA83, LF and EF) were purchased from List laboratories.

Construction of Mutant Fabs from 35PA83

A variant was first constructed in order to humanize the 35PA83 immunoglobulin fragment. This variant was obtained by carrying out the mutations described in the tables below:

TABLE 4

Mutations for humanization of the 35PA83 heavy chain

| Amino acid position | 35PA83 | Hu35PA83 |
|---|---|---|
| 1 | None | Q |
| 2 | None | V |
| 3 | None | Q |
| 4 | None | L |
| 5 | None | Q |
| 6 | None | E |
| 7 | None | S |

TABLE 5

Mutations for humanization of the 35PA83 light chain

| Amino acid position | 35PA83 | Hu35PA83 |
|---|---|---|
| 1 | None | A |
| 2 | None | I |
| 3 | None | Q |
| 4 | None | L |

Using this humanized variant, mutant sequences derived from the 35PA83 gene were then generated by a circular mutagenizing amplification technology, Massive Mutagenesis® (Biométhodes, Evry, France). The mutations were introduced into the CDRs of the heavy and light chains using NNS codons (N encodes A, T, G or C, and S encodes G or C). The CDR regions were defined according to Kabat et al. (Wu and Kabat, 1970) and IMGT (Lefranc, Pommie et al., 2003).

The DNA obtained was used to transform SURE cells by electroporation. After addition of SB medium supplemented with carbenicillin to the culture and incubation for 1 h at 37° C., 1 ml of VCSM13 helper phage (Andris-Widhopf et al., 2001) (about 1012 pfu) was added to the culture. After incubation for 2 h, 70 μg/ml of kanamycin were added and the culture was shaken over night.

Selection of Immunoglobulins by Phage Display

The phage-immunoglobulin particles were purified and concentrated from 50 ml of culture by precipitation with polyethylene glycol (PEG), then resuspended in 3 ml of PBS-1% BSA-0.02% azide and filtered on a 0.45 μm filter. The titer of this phage preparation was approximately 1010 pfu/ml. The phage-immunoglobulins were subjected to three infection-selection-recovery cycles, corresponding to 5, 10 and 15 washes respectively, as previously described (Andris-Widhopf, Rader et al., 2000).

Expression, Periplasmic Extraction and Purification of Soluble Mutant Fabs

Each DNA variant was transformed in bacteria of the *E. coli* strain HB2151, rendered chemically competent. The cells were cultured at 30° C., and shaken at 250 rpm in 1 l of SB medium containing 50 μg/ml of carbenicillin and 0.1% of glucose. When the culture reached an absorbance at λ=600 nm of 1.5, induction with 1 mM of IPTG (isopropyl β-D-1-thiogalactopyranoside) was carried out for 18 h at 22° C.

The immunoglobulin fragments were extracted with polymyxin B sulfate (Sigma) and purified on a nickel column (Ni-NTA spin column, Qiagen, Valencia, Calif.) according to the manufacturer's instructions, then dialyzed with 1×PBS at 4° C. for 3 h.

Quantification of the Soluble Fab

The purity of the Fab was tested by SDS-PAGE and its concentration was determined using the Quantity One® software (Biorad).

Real-Time Measurement of Surface Plasmon Resonance (SPR)

The kinetic constants for the interaction between PA83 and the 35PA83 variants were determined using the Biacore X SPR system (BIAcore, Uppsala, Sweden). The PA83 was immobilized on a CM5 sensitive chip (Biacore) using a procedure for coupling of amines by injection of 30 μl of 2 μg/ml of PA83 in 10 mM of sodium acetate, pH 4.5. To minimize the probability of rebinding, the $K_D$ was measured using a high flow rate (30 μl/min) and a minimum amount of coupled antigen (approximately 500 RU, resonance units). The degree of binding of various Fab concentrations ranging from 5 to 400 nM in PBS was determined at a flow rate of 30 l/min. The binding data was introduced into a 1:1 langmuir model of the BIA evaluation software (Biacore). The association and dissociation constants ($k_{on}$ and $k_{off}$ respectively) for the binding of the Fab to PA83 were determined at 35° C.

Sequence Analysis

The sequences of the heavy and light chains of the clones selected were determined by Genome Express (Meylan, France) using the ompseq and newpelseq primers (Andris-Widhopf, Rader et al., 2000). The sequences were analyzed on line, using the IMGT system.

Among the clones selected, the 35PA83 "6.20" variant was identified.

The heavy-chain variable region (VH) of the "6.20" variant (SEQ ID No.: 1) has 2 mutations compared with that of the humanized 35PA83 Fab: H-L (residue 54 according to the IMGT nomenclature) and S-G (residue 74 according to the IMGT nomenclature).

The light-chain variable region (VL) of the "6.20" variant (SEQ ID No.: 2) has 1 mutation compared with that of the humanized 35PA83 Fab: Q-L (residue 68 according to the IMGT nomenclature).

Construction of the ATH-GA Expression Vector for Expression of the 35PA83 "6.20" Immunoglobulin A sequence encoding the MB7 optimized signal peptide (SEQ ID No.: 19, MRWSWIFLLLLSITSANA)

was added in the N-terminal position of the two sequences encoding the variable parts of, respectively, the heavy chain and the light chain of the 35PA83 "6.20" variant (SEQ ID Nos: 7 and 8). These sequences were optimized and synthesized by GeneArt (Regensburg, Germany).

The sequences of the heavy and light chains of the variant were then cloned into the HK gen EFss vector in order to obtain the ATH-GA vector.

The sequencing of the ATH-GA vector was carried out according to the Sanger technique (or chain termination method, ref.: Sanger F. et al, 1977, PNAS 74: 5463). The sequencings were carried out by Eurofins MWG Operon (Ebersberg, Germany) according to the "GLP" regulatory quality level. This involves the maximum quality level, with double-stranded coverage of the DNA sequence, a 2-fold minimum redundancy, accuracy greater than 99.999%, dedicated instruments, the drafting of a quality report and archiving of the documents generated.

The ATH-GA vector preparation was stored in TE buffer (10 mM Tris pH 8 and 1 mM EDTA) at −20° C. before adjustment to the concentration of 1 µg/µl for transfection into the YB2/0 cell lines.

Example 2: Obtaining of Transformants Producing the 35PA83 "6.20" Immunoglobulin The 35PA83 "6.20" antibody was produced in the YB2/0 lines. For the experiments below, the ELISA technique implemented is carried out according to the following conditions:
96-well microtitration plates (maxisorp, Nunc, Denmark) are coated with PA diluted in PBS (5 µg/ml, 100 µl per well), over night at 4° C. The plates are blocked by adding 200 µl of PBS-5% BSA at 37° C. for 1 hour, and sera serially diluted in PBS-0.1% Tween 20-1% BSA are incubated (100 µl per well) at 37° C. for 2 hours. An anti-mouse IgG alkaline phosphatase conjugate or an anti-human IgG alkaline phosphatase conjugate (Sigma) is incubated (1/10 000) at 37° C. for 1 hour. A p-nitrophenyl phosphate substrate is then incubated for 30 minutes at ambient temperature. The results are determined by measuring the absorbance at 405 nm with an automated microplate reader (iEMS reader MF, Labsystems, Helsinki, Finland). The final dilution point, the reversion of which determines the titer of the serum, is determined as giving a signal less than or equal to 2 times the naive serum used for the negative control.
a. Transformation Level The ATH-GA vector was introduced into the YB2/0 host cell line by electroporation. After selective culturing (with the G418 selective agent), pools of transfectants were obtained and plated out in a semi-solid medium in the presence of fluorescent anti-human IgG antibody and under conditions allowing the growth of isolated colonies. The fluorescence intensity of the colonies, proportional to their production capacity, was analyzed using the ClonePixFL automated device (CPFL) and the colonies exhibiting the greatest fluorescence were sub-cultured by the automated device.

b. Transformant Selection

Production level: first screening of transformants which are stronger producers

The production of human IgGs was determined by the ELISA technique on the supernatants of the double-selection P96 wells containing the cells in order to perform a first hierarchization of the cloids with regard to their production capacities.

Three successive screenings (every 2-3 days) were carried out and the 10 best producers of each screening were selected. Out of 528 transformants, 27 were pursued and maintained in P24 and a study of their productivity at D+3 and of their maximum production (D+7) was carried out in parallel.

Productivity at D+3 and maximum production (D+7)

The best producer clones selected with a productivity mostly greater than 5 pcd and a maximum production greater than 10 µg/ml were subjected to cell amplification in selective medium (double selection) for saving in liquid nitrogen.

c. Selection of a Clone and Production of the 35PA83 "6.20" Immunoglobulin in a Cell Cultivator A clone was retained for the production of the 35PA83 "6.20" immunoglobulin in a cell cultivator (10 L) as a function of its growth and productivity characteristics.

The 35PA83 immunoglobulin was produced, concentrated and purified.

Example 3: N-Glycosylation Profile of 35PA83 "6.20"

An assay of the fucose level was carried out by the ELISA technique on the supernatants of the cloids selected at D+3 and D+7.

Figure 3:
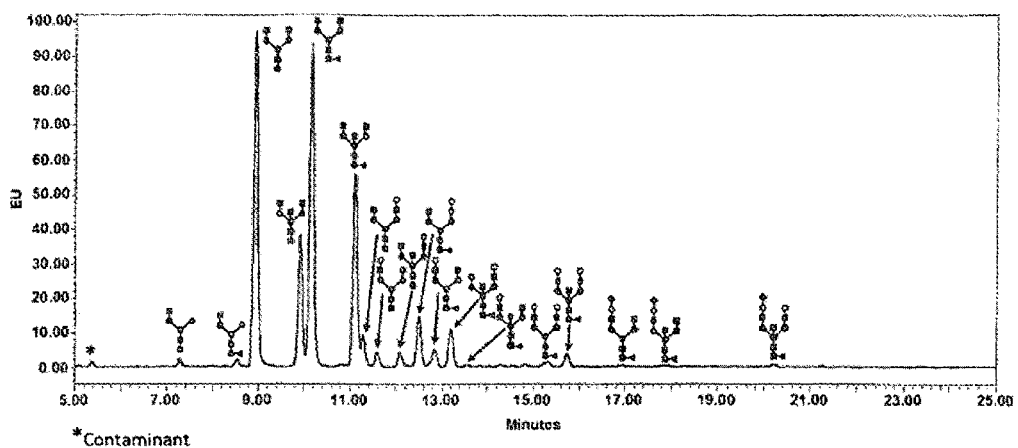

In order to determine the N-glycosylation profile of the 35PA83 "6.20" immunoglobulins, the latter were treated enzymatically using peptidyl-N-glycosidase (PNGase F). Quantitative profiling of the N-glycan mixture was then carried out by ultra performance liquid chromatography in HILIC mode (UPLC/FD).
Results:

FIG. 3 shows the N-glycosylation profile of the 35PA83 "6.20" immunoglobulins. Table 6 compiles a list of the major species identified, modified by their relative molar ratio (RMR, %), the degree of fucosylation (Fuc), the level of intercalated GlcNAc (Bis-GlcNAc) and the degree of sialylation, and also the galactosylation index (Gal).

TABLE 6

| Abbreviations | Glycan structures |
|---|---|
| G0-Gn | 0.7 |
| G0F-Gn | 0.7 |
| G0 | 26.4 |

TABLE 6-continued

| Abbreviations | Glycan structures |
|---|---|
| G0B | 10.7 |
| G0F | 26.2 |
| Man5 | 0.0 |
| G0FB | 15.8 |
| G1(1,6) | 2.7 |
| G1(1,3) | 1.5 |
| G1(1,6)B | 1.4 |
| G1(1,3)B | 0.0 |
| G1(1,6)F | 4.4 |
| G1(1,3)F | 1.9 |
| G1(1,6)FB | 3.3 |
| G1(1,3)FB | 0.3 |
| G2 | 0.0 |
| G2B | 0.2 |
| G2F | 0.6 |
| G2FB | 1.5 |
| G1(1,3)NeuAc1 | 0.0 |
| G1(1,3)FNeuAc1 | 0.3 |
| G1(1,3)FBNeuAc1 | 0.3 |
| G2(1,3)NeuAc1 | 0.0 |
| G2(1,3)BNeuAc1 | 0.0 |
| G2F(1,3)NeuAc1 | 0.0 |
| G2FB(1,3)NeuAc1 | 0.4 |
| G2NeuAc2 | 0.0 |
| G2BNeuAc2 | 0.0 |
| G2FNeuAc2 | 0.0 |
| G2FBNeuAc2 | 0.0 |
| Unidentified peak | 0.6 |
| Degree of fucosylation (%) | 40 |
| Galactosylation index (%) | 22 |
| Level of Bis-GlcNAc (%) | 34 |

The 35PA83 immunoglobulin is characterized by a glycosylation profile which is strictly of biantennary complex type with predominantly agalactosylated structures of G0 type (≈80%) the pentasaccharide nucleus of which is possibly substituted with a fucose residue (G0F), an intercalated GlcNAc residue (G0B), or both (G0FB). Mono- and bigalactosylated structures of G1,2(F)(B) type which may or may not be sialylated are also observed in low abundance (≈80%), with an N-glycan galactosylation index of 22%. The degree of fucosylation of the N-glycans is 40%, while the level of intercalated GlcNAc structures is 34%.

Example 4: Measurement of the Kinetic Constants of the 35PA83 "6.20" Immunoglobulin After the production of 35PA83 "6.20" immunoglobulin in YB2/0 cells, the cell culture supernatant is recovered, concentrated 15 times, and then subjected to affinity chromatography by means of a recombinant protein A-Sepharose. A second purification step is carried out by means of the HiPrep 16/10 SP FF cation exchange column. The integrity of the immunoglobulin purified and the absence of contaminant are verified by SDS-PAGE and by ELISA for the binding to recombinant PA83.

The affinity constants are measured by surface plasmon resonance (SPR) by means of the Biacore™ SPR Systems (Biacore Uppsala, Sweden). PA83 (List Biological Laboratories, Inc., Campbell, Calif.) is immobilized at a maximum of 210 RU on a CM5 chip (Biacore™ SPR Systems) by means of an amine bond, according to the supplier's instructions. A flow of 30 µl/min is maintained during the measurement. For each measurement, a minimum of 6 dilutions of immunoglobulin in HBS-EP buffer (Biacore™ SPR Systems), with concentrations of between 10 and 0.1 µg/ml, are tested for 1900 seconds. After each immunoglobulin dilution, the chip is regenerated with glycine, pH 1.5 (Biacore™ SPR Systems), with a flow of 10 µl/min for 30 seconds. The affinity constants are calculated by means of a bivalent analyte method (Karlsson et al. 1991), and verified with tests of internal consistency (Schuck et al. 1996).

Results:

The 35PA83 "6.20" immunoglobulin exhibits, with respect to the PA83 antigen, an association constant (Ka) of $2.93\times10^5$ M, a dissociation constant ($K_d$) of $9.70\times10^{-6}$ M and an affinity constant ($K_D$) of $3.3\times10^{-11}$ M.

Example 5: Measurement of the Neutralizing Effect of 35PA83 "6.20"

The in vitro neutralization test is carried out according to the protocol described by Little et al. (Little et al., 1990). The J774A.1 mouse macrophage cell line (ATCC-TIB67) is cultured in untreated culture flasks in order to grow in suspension. The cells are sub-cultured twice a week in IMDM medium, 10% FCS, at $0.3\times10^6$ cells/ml.

The toxic activity is obtained by extemporaneously mixing PA (List Biological Laboratories, Inc.) and LF (List Biological Laboratories, Inc.). A cell suspension at $5\times10^5$ cells/ml in IMDM without phenol red, containing 5% of FCS, is distributed into a round-bottomed microplate in a proportion of 200 µl/well. After 16 h at 37° C., 5% $CO_2$, the adherent cells form a carpet of cells in monolayer.

D0:

Elimination of the culture medium (elimination of the LDH spontaneously released during the culture).

Preparation of the concentration ranges of PA 100 ng/ml constant+LF variable concentration (100-50-25-12.5-6.25-3.12-1.6-0.78 ng/ml).

Preparation of the concentration ranges of LF 100 ng/ml constant+PA variable concentration (100-50-25-12.5-6.25-3.12-1.6-0.78 ng/ml).

200 µl of each of the toxin mixture concentrations are distributed per well, the plate is incubated for 4 h at 37° C.

In order to test the neutralizing capacity of the anti-PA antibody, a fixed concentration of toxic mixture is chosen and is pre-incubated for 1 h at 37° C. with a series of dilution of the antibody, then distributed into the plate.

A range of cell lysis induced by 1% Triton X100 and representing 100-75-50-25-12.5-6.25 and 0% lysis.

The samples are deposited in triplicate.

D0+4h:

The concentration of LDH released by the lysis of the cells is measured according to the instructions of the Cyto Tox 96 Non-radioactive Cytotoxic Assay kit from Promega.

The optimal concentrations of PA and LF are determined by carrying out a dose-effect of PA in the presence of a fixed concentration of LF and a dose-effect of LF in the presence of a fixed concentration of PA.

The EC50 values are, for PA, 31 and 32 ng/ml in the presence of 100 ng/ml of LF, and, for LF, 6.5 and 6.2 ng/ml in the presence of 100 ng/ml of PA.

The combination of 100 ng/ml of PA with 100 ng/ml of LF makes it possible to obtain a maximum cell lysis close to 80%.

The neutralizing activity of the anti-PA antibody is determined by its capacity to bind to PA and to thus block the binding of PA to the cell receptors.

The toxin, consisting of the mixture of 100 ng/ml of PA and 100 ng/ml of LF, is incubated in the presence of various concentrations of anti-PA antibody for 1 h at 37° C. 200 µl of the mixture are then deposited in triplicate in the wells containing the J774A.1 cells.
Results:

The neutralizing effect of the 35PA83 "6.20" antibody was evaluated in 2 series of tests under the following conditions:

Series 1: anti-PA antibody concentration: 50-10-2-0.4-0.08-0.016-0.0032-0 ng/ml.

Series 2: anti-PA antibody concentration: 50-15.01-4.51-1.35-0.406-0.1220-0.037-0 ng/ml.

Under these conditions, the anti-PA neutralizes the effect of the PA/LF toxin in a dose-dependent manner and completely inhibits cell mortality at concentrations above 10 ng/ml.

The 50% neutralization value ($EC_{50}$) is determined for the 35PA83 "6.20" immunoglobulin; it is around 4-5 ng/ml.

Example 6: Pharmacokinetic Studies

In order to evaluate the half-life time of the 35PA83 "6.20" immunoglobulin, six six-week-old A/J mice (Harlan, Gannat, France) were divided up into two subgroups of equal size. All the mice received the 35PA83 "6.20" immunoglobulin, administered by means of a single subcutaneous injection at the dose of 10 mg/kg. The blood was collected by daily retro-orbital puncture, from day 1 and up to day 6 after injection, and then from day 8 up to day 10 after injection, alternating between the mice on each separate day. The half-life time of the 35PA83 "6.20" immunoglobulin was established on the basis of the results of the ELISA assays carried out on the pools of serum samples, after linear extrapolation of the values obtained.

In order to carry out the ELISA assays, the wells of 96-well microtitration plates were coated by incubation with the PA83 antigen or the LF antigen (List Biological Laboratories, Inc.) diluted in PBS buffer (5 µg/ml, 100 µl per well) over night at 4° C. The free sites of the microplate wells were then blocked by incubation with a volume of 200 µl of a solution of bovine serum albumin (BSA) at 5% in PBS buffer, for 1 hour at 37° C. The sera were serially diluted in a PBS buffer containing 0.1% of Polysorbate 20 (Tween® 20) and 1% of BSA, then incubated in the plates (100 µl/well) for 2 hours at 37° C. The wells of the plates were then incubated with an anti-mouse IgG/alkaline phosphatase conjugate or an anti-human IgG/alkaline phosphatase conjugate diluted to 1/10 000 (Sigma, Saint Louis, Mo., United States), for 1 hour at 37° C. The p-nitrophenyl phosphate substrate (Sigma) was then added and the plates were then incubated for 30 minutes at ambient temperature. The absorbance at 405 nm was determined using an automatic microplate reader (iEMS Reader MF, Labsystems, Helsinki, Finland). The limiting dilution point, the reciprocal value of which corresponds to the antibody titer of the serum, was defined as the point for which the value of the signal was equal to double the value of the signal measured for the serum of naive mice. The serum of naive mice is used as a negative control.

Example 7: Study of Passive Protection of Rats

For the in vivo trials, Fischer rats (250 to 300 g) (C. River, L'Abresle, France) are injected with 40 µg of PA (List Biological Laboratories, Inc., Campbell, Calif.) and 8 µg of LF per 250 g of rat, in the manner described in Ezzell et al. (Ezzell et al., 1984), except for the fact that the tail vein is used. 4 animals are used per group and, for the evaluation of the 35PA83 "6.20" immunoglobulin, the immunoglobulin is added to the PA and to the LF before the injection. The rats are observed twice a day for 10 days. All the in vivo trials presented in this study are approved by the local ethics committee for animal experiments and animal care.
Preparation and Use of Sterne Spores:

Spores of B. anthracis Sterne (Pasteur collection) are prepared as set out in Albrecht et al. (Albrecht et al., 2007) and kept frozen (−20° C.). The spores are counted by viable plate counting after freezing/thawing and the count is verified when each tube is used in this study. The LD50 of these spores administered intravenously to 9-week-old male A/J mice (Harlan, Gannat, France), weighing 20-25 g, is established at $1\times10^4$, leading to death in 48 to 72 hours, that is to say close to a value of 2×10(4) used in another study (Albrecht et al., 2007).

Example 8: Prophylaxis Using the 35PA83 "6.20" Immunoglobulin, Short Treatment with Tetracycline, or Both For the studies of a prophylactic scheme of the 35PA83 "6.20" immunoglobulin or using tetracycline only, the immunoglobulins are injected into groups of 10 A/J mice, subcutaneously, 12 hours before the infection (an injection of 5 mg/kg or of 2 mg/kg). The challenge is administered as 10 000 $LD_{50}$ or $1\times10^8$ spores and the mice are observed twice a day for 2 weeks, then 5 times a week for an additional 2 weeks. The surviving mice are retested by infection one month later, with the same amount of spores, and observed for an additional month. For the studies of a prophylactic scheme involving both tetracycline and the 35PA83 "6.20" immunoglobulin, groups of 10 mice are treated with tetracycline as in the scheme involving tetracycline alone, but, in addition, the 35PA83 "6.20" immunoglobulin is injected 12 hours before the challenge. For the active protection studies, 10 mice are injected subcutaneously with 5 µg of PA per mouse, in complete Freund's adjuvant. A second group receives the same injection and then, 1 month later, the immune response of this group is stimulated with the same dose of PA in incomplete Freund's adjuvant.

Example 9: Prophylaxis Using the 35PA83 "6.20" Immunoglobulin, Short Treatment with Doxycycline, or Both The study of prophylaxis with doxycycline, with or without the 35PA83 "6.20" immunoglobulin, was carried out with groups of ten 10-week-old A/J mice (Harlan, Gannat, France), which were injected prophylactically with the antibiotic intraperitoneally, at the single daily dose of 5 mg/kg. The chemoprophylaxis was begun 12 hours before the infection and was carried out for 7 days, thereby representing a 9/10 reduction in the standard duration, which is 60 days.

A doxycycline dosage which is approximately double the standard human dosage was chosen (daily dosage of 3 mg/kg for an adult human), and it has been shown that smaller doses are effective against B. anthracis (Friedlander et al., 1993, J Infect Dis, Vol. 167: 1239-1243; Kalns et al., 2002, Biochem Biophys Res Commun, Vol. 297: 506-509). Larger doses have been used (Heine et al., 2007, Antimicrob Agents Chemother, Vol. 51: 1373-1379); it was, however, observed that a dose of 50 mg/kg appeared to be poorly tolerated in the A/J mice, which then exhibited swelling of the abdomen and hair standing on end. In order to supplement the doxycycline treatment with the 35PA83 "6.20" immunoglobulin, a single dose of this antibody (1 or 2 mg/kg) was optionally injected concomitantly with the final dose of doxycycline. The infection used 1×10$^8$ intraperitoneally injected spores, which represents 10 000 LD$_{50}$. The mice were observed twice a day for the first two weeks, then five times per week for an additional two weeks.

Example 10: Therapy with the 35PA83 "6.20" Immunoglobulin, Short Treatment with Ciprofloxacin, or Both For the therapeutic scheme studies, groups of 10 A/J mice are challenged with a dose of 1000 LD50 or 1×10$^7$ spores. After 12 hours, the 35PA83 "6.20" immunoglobulin (subcutaneously, 1 injection of 10 mg/kg) or the ciprofloxacin (subcutaneously, 50 mg/kg twice a day for 5 days) is injected separately or the ciprofloxacin and the 35PA83 "6.20" immunoglobulin are both injected on the first day, and then the ciprofloxacin alone is again injected for 4 additional days.

Example 11: Therapy with the 35PA83 "6.20" Immunoglobulin, Short Treatment with Ciprofloxacin, or Both (Other Trial)

For the curative treatment studies, groups of 10 A/J mice are infected with a dose of 1000 LD$_{50}$ or 1×10$^7$ spores. After 12 hours, the mice were treated with ciprofloxacin (subcutaneously, with an initial injection of 25 mg/kg) or with the 35PA83 "6.20" IgG (subcutaneously, 1 injection of 10 mg/kg) separately; or ciprofloxacin and the 35PA83 "6.20" IgG are both injected simultaneously at two different sites. Additional periods of 24 hours and 48 hours before beginning the combined treatment (ciprofloxacin and 35PA83 "6.20" IgG) were also tested. After the first administration of the treatment, ciprofloxacin alone (25 mg/kg, twice a day) was injected for the following 4.5 days. The ciprofloxacin dose was chosen to be approximately double the standard dose in humans (daily dose of 20 mg/kg in adult humans), this dose having already been used effectively against *B. anthracis* (Kalns et al., 2002, Biochem Biophys Res Commun, Vol. 297: 506-509). The tolerance at this selected dose was favorably tested in the A/J mice before beginning this study. This part of the study aims essentially to solve the problem of short-term survival following a delayed treatment, and the monitoring was limited to the period of 18 days following the infection.

Example 12: Comparison Between the Passive and Active Prophylactic Anti-Anthrax Treatments A passive prophylactic anti-anthrax treatment consists of a treatment with the 35PA83 "6.20" immunoglobulin. An active prophylactic anti-anthrax treatment consists of a treatment by immunization with the PA antigen.

In order to compare the active and passive immunoprotection, a group of ten mice was immunized subcutaneously with 5 µg of PA83 in complete Freund's adjuvant and infected intraperitoneally with 10 000 LD$_{50}$, one month later. Another group of ten mice was immunized in an identical manner, but received a booster immunization four weeks later with 5 µg of PA83 in incomplete Freund's adjuvant, and infected one month after the second injection. In parallel, the passive protection by the 35PA83 "6.20" immunoglobulin against the same infection was evaluated. All the infected animals were observed for one month, and the results of the two types of prophylaxis were compared.

Example 13: Comparison Between a Passive Immunization and a Late Treatment with the 35PA83 "6.20" IgG Only in White New Zealand (WNZ) Rabbits Infected with Spores of 9602

For the passive immunization study, the 35PA83 "6.20" IgG is injected intravenously at 2.5, 1 and 0.5 mg/kg in 3 groups of 8 WNZ rabbits, anesthetized beforehand with the anesthetic IMALGENE®1000 (Merial, Lyon, France). Five minutes later, the animals are brought into contact with 25 µl of a suspension of spores of the *B. anthracis* virulent strain 9602, deposited on each nostril for inhalation into the lungs, and corresponding to 100 LD$_{50}$.

For the late treatment, the same experimental conditions were used, except that 2 groups of 8 animals receive the injection of IgG (2.5 mg/kg) 6 h after being brought into contact with 80 LD$_{50}$ or 200 LD$_{50}$ of *B. anthracis* 9602 spores.

For each group, 4 additional animals are used under the same experimental conditions, as positive controls. All the experiments with the *B. anthracis* 9602 strain are carried out in a security level 3 laboratory, and the animals are observed 21 days after the bringing into contact.

LITERATURE REFERENCES

Albrecht, M. T., H. Li, E. D. Williamson, C. S. Lebutt, H. C. Flick-Smith, C. P. Quinn, H. Westra, D. Galloway, A. Mateczun, S. Goldman, H. Groen, and L. W. Baillie. 2007. Human monoclonal antibodies against anthrax lethal factor and protective antigen act independently to protect against *Bacillus anthracis* infection and enhance endogenous immunity to anthrax. Infect Immun.

Andris-Widhopf, J., C. Rader, P. Steinberger, R. Fuller, and C. F. Barbas, 3rd. 2000. Methods for the generation of chicken monoclonal antibody fragments by phage display. J Immunol Methods 242:159-181.

Andris-Widhopf, J., P. Steinberger, R. Fuller, C. Rader, and C. F. Barbas, 3rd. 2001. Generation of antibody libraries: PCR amplification and assembly of light- and heavy-chain coding sequences. In C. F. Barbas, 3rd, D. R. Burton, J. K. Scott, and G. J. Silverman (ed.), Phage Display: A Laboratory Manual. Cold Spring Harbor Laboratory Press, New York.

Carter, P., H. Bedouelle, and G. Winter. 1985. Improved oligonucleotide site-directed mutagenesis using M13 vectors. Nucleic Acids Res 13:4431-43. Ezzell, J. W., B. E. Ivins, and S. H. Leppla. 1984. Immunoelectrophoretic analysis, toxicity, and kinetics of in vitro production of the protective antigen and lethal factor components of *Bacillus anthracis* toxin. Infect Immun 45:761-7.

Karlsson, R., A. Michaelsson, and L. Mattsson. 1991. Kinetic analysis of monoclonal antibody-antigen interactions with a new biosensor based analytical System. J Immunol Methods 145:229-40).

Laffly, "Selection of a macaque Fab with framework regions like those in humans, high affinity, and ability to neutralize the protective antigen (PA) of *bacillus anthracis* by binding to segment of PA between residues 686 and 694", Antimicrobial agents and chemotherapy, August 2005, p. 3414-3420.

Little, S. F., S. H. Leppla, and A. M. Friedlander. 1990. Production and characterization of monoclonal antibodies against the lethal factor component of *Bacillus anthracis* lethal toxin. Infect Immun 58:1606-13.

Schuck, P., and A. P. Minton. 1996. Analysis of mass transport-limited binding kinetics in evanescent wave biosensors. Anal Biochem 240:262-72.

The invention claimed is:

1. A class-G immunoglobulin directed against the anthrax toxin protective antigen, wherein
   each heavy chain of the immunoglobulin comprises, or consists of, SEQ ID NO:5, and
   each light chain of the immunoglobulin comprises, or consists of, SEQ ID NO:6.

2. The immunoglobulin of claim 1, wherein said heavy chain and/or said light chain is bonded to a signal peptide.

3. The immunoglobulin of claim 1, wherein:
   each of the heavy chains comprises SEQ ID NO:7, and
   each of the light chains comprises SEQ ID NO:8.

4. The immunoglobulin of claim 1 having on its Asn297 glycosylation site N-glycans having a degree of fucosylation less than 65%.

5. The immunoglobulin of claim 4, having on its Asn297 glycosylation site a glycan structure of biantennary type, with short chains and a low degree of sialylation, having non-intercalated end mannoses and/or end N-acetylglucosamines.

6. The immunoglobulin of claim 5, having a content of greater than 60% for G0+G1+G0F+G1F forms, wherein G0F+G1F forms are less than 50%.

7. The immunoglobulin of claim 5, having a content of greater than 60% for G0+G1+G0F+G1F forms, and wherein fucose content is less than 65%.

8. The immunoglobulin of claim 5, having a content of less than 40% for G1F+G0F forms.

* * * * *

SEQUENCE LISTING

<160> NUMBER OF SEQ ID NOS: 20

<210> SEQ ID NO 1
<211> LENGTH: 125
<212> TYPE: PRT
<213> ORGANISM: Artificial Sequence
<220> FEATURE:
<223> OTHER INFORMATION: Heavy chain variable region

<400> SEQUENCE: 1

Gln Val Gln Leu Gln Glu Ser Gly Pro Gly Leu Leu Lys Pro Ser Glu
1               5                   10                  15

Thr Leu Ser Leu Thr Cys Ala Val Ser Gly Asp Ser Ile Ser Gly Gly
            20                  25                  30

Tyr Tyr Trp Ser Trp Ile Arg Gln Ser Pro Gly Lys Gly Leu Glu Trp
        35                  40                  45

Ile Gly Leu Ile Tyr Gly Ser Thr Ala Asp Thr Arg Tyr Asn Pro Ser
    50                  55                  60

Leu Lys Gly Arg Val Thr Ile Ser Lys Asp Thr Ser Lys Asn Gln Leu
65                  70                  75                  80

Ser Leu Gln Leu Arg Ser Val Thr Ala Ala Asp Thr Ala Val Tyr Tyr
                85                  90                  95

Cys Ala Arg Ser Gly Tyr Asn Phe Trp Ser Gly Glu Tyr Tyr Gly Leu
            100                 105                 110

Asp Ser Trp Gly Gln Gly Ala Val Val Thr Val Ser Ser
        115                 120                 125

<210> SEQ ID NO 2
<211> LENGTH: 107
<212> TYPE: PRT
<213> ORGANISM: Artificial Sequence
<220> FEATURE:
<223> OTHER INFORMATION: Light chain variable region

<400> SEQUENCE: 2

Ala Ile Gln Leu Thr Gln Ser Pro Ser Ser Leu Ser Ala Tyr Val Gly
1               5                   10                  15

Asp Lys Val Thr Ile Thr Cys His Ala Ser Gln Gly Ile Asn Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Leu Ser Gly Val Pro Ser Arg Phe Ser Gly
    50                  55                  60

Ser Gly Ser Gly Thr Asp Tyr Thr Leu Thr Ile Ser Ser Leu Gln Ser
65                  70                  75                  80

Glu Asp Phe Ala Ser Tyr Tyr Cys Leu Gln Tyr Asp Ser Ala Pro Leu
                85                  90                  95

Ala Phe Gly Pro Gly Thr Lys Leu Asp Ile Lys
            100                 105

<210> SEQ ID NO 3
<211> LENGTH: 330
<212> TYPE: PRT
<213> ORGANISM: Artificial Sequence
<220> FEATURE:
<223> OTHER INFORMATION: Heavy chain constant region

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 4
<211> LENGTH: 107
<212> TYPE: PRT
<213> ORGANISM: Artificial Sequence
<220> FEATURE:
<223> OTHER INFORMATION: Light chain constant region

<400> SEQUENCE: 4

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

```
Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 5
<211> LENGTH: 455
<212> TYPE: PRT
<213> ORGANISM: Artificial Sequence
<220> FEATURE:
<223> OTHER INFORMATION: Complete heavy chain without signal peptide

<400> SEQUENCE: 5

Gln Val Gln Leu Gln Glu Ser Gly Pro Gly Leu Leu Lys Pro Ser Glu
 1               5                   10                  15

Thr Leu Ser Leu Thr Cys Ala Val Ser Gly Asp Ser Ile Ser Gly Gly
             20                  25                  30

Tyr Tyr Trp Ser Trp Ile Arg Gln Ser Pro Gly Lys Gly Leu Glu Trp
             35                  40                  45

Ile Gly Leu Ile Tyr Gly Ser Thr Ala Asp Thr Arg Tyr Asn Pro Ser
 50                  55                  60

Leu Lys Gly Arg Val Thr Ile Ser Lys Asp Thr Ser Lys Asn Gln Leu
 65                  70                  75                  80

Ser Leu Gln Leu Arg Ser Val Thr Ala Ala Asp Thr Ala Val Tyr Tyr
                 85                  90                  95

Cys Ala Arg Ser Gly Tyr Asn Phe Trp Ser Gly Glu Tyr Tyr Gly Leu
            100                 105                 110

Asp Ser Trp Gly Gln Gly Ala Val Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
            290                 295                 300
```

```
Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
            325                 330                 335

Pro Ala Pro Ile Glu Lys Thr Ile Ser Lys Ala Lys Gly Gln Pro Arg
        340                 345                 350

Glu Pro Gln Val Tyr Thr Leu Pro Pro Ser Arg Asp Glu Leu Thr Lys
    355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
            405                 410                 415

Lys Leu Thr Val Asp Lys Ser Arg Trp Gln Gln Gly Asn Val Phe Ser
        420                 425                 430

Cys Ser Val Met His Glu Ala Leu His Asn His Tyr Thr Gln Lys Ser
    435                 440                 445

Leu Ser Leu Ser Pro Gly Lys
450                 455

<210> SEQ ID NO 6
<211> LENGTH: 214
<212> TYPE: PRT
<213> ORGANISM: Artificial Sequence
<220> FEATURE:
<223> OTHER INFORMATION: Complete light chain without signal peptide

<400> SEQUENCE: 6

Ala Ile Gln Leu Thr Gln Ser Pro Ser Ser Leu Ser Ala Tyr Val Gly
1               5                   10                  15

Asp Lys Val Thr Ile Thr Cys His Ala Ser Gln Gly Ile Asn Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Leu Ser Gly Val Pro Ser Arg Phe Ser Gly
    50                  55                  60

Ser Gly Ser Gly Thr Asp Tyr Thr Leu Thr Ile Ser Ser Leu Gln Ser
65                  70                  75                  80

Glu Asp Phe Ala Ser Tyr Tyr Cys Leu Gln Tyr Asp Ser Ala Pro Leu
                85                  90                  95

Ala Phe Gly Pro Gly Thr Lys Leu Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 7
<211> LENGTH: 473
<212> TYPE: PRT
<213> ORGANISM: Artificial Sequence
<220> FEATURE:
<223> OTHER INFORMATION: Heavy chain with signal peptide

<400> SEQUENCE: 7

Met Arg Trp Ser Trp Ile Phe Leu Leu Leu Ser Ile Thr Ser Ala
1               5                   10                  15

Asn Ala Gln Val Gln Leu Gln Glu Ser Gly Pro Gly Leu Leu Lys Pro
            20                  25                  30

Ser Glu Thr Leu Ser Leu Thr Cys Ala Val Ser Gly Asp Ser Ile Ser
            35                  40                  45

Gly Gly Tyr Tyr Trp Ser Trp Ile Arg Gln Ser Pro Gly Lys Gly Leu
    50                  55                  60

Glu Trp Ile Gly Leu Ile Tyr Gly Ser Thr Ala Asp Thr Arg Tyr Asn
65                  70                  75                  80

Pro Ser Leu Lys Gly Arg Val Thr Ile Ser Lys Asp Thr Ser Lys Asn
                85                  90                  95

Gln Leu Ser Leu Gln Leu Arg Ser Val Thr Ala Ala Asp Thr Ala Val
            100                 105                 110

Tyr Tyr Cys Ala Arg Ser Gly Tyr Asn Phe Trp Ser Gly Glu Tyr Tyr
            115                 120                 125

Gly Leu Asp Ser Trp Gly Gln Gly Ala Val Val Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

```
Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
                420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
        450                 455                 460

Lys Ser Leu Ser Leu Ser Pro Gly Lys
465                 470

<210> SEQ ID NO 8
<211> LENGTH: 232
<212> TYPE: PRT
<213> ORGANISM: Artificial Sequence
<220> FEATURE:
<223> OTHER INFORMATION: Light chain with signal peptide

<400> SEQUENCE: 8

Met Arg Trp Ser Trp Ile Phe Leu Leu Leu Leu Ser Ile Thr Ser Ala
1               5                   10                  15

Asn Ala Ala Ile Gln Leu Thr Gln Ser Pro Ser Ser Leu Ser Ala Tyr
                20                  25                  30

Val Gly Asp Lys Val Thr Ile Thr Cys His Ala Ser Gln Gly Ile Asn
            35                  40                  45

Ser Trp Leu Ala Trp Tyr Gln Gln Lys Pro Lys Ala Pro Lys Leu
        50                  55                  60

Leu Ile Tyr Lys Ala Ser Ser Leu Leu Ser Gly Val Pro Ser Arg Phe
65                  70                  75                  80

Ser Gly Ser Gly Ser Gly Thr Asp Tyr Thr Leu Thr Ile Ser Ser Leu
                85                  90                  95

Gln Ser Glu Asp Phe Ala Ser Tyr Tyr Cys Leu Gln Tyr Asp Ser Ala
                100                 105                 110

Pro Leu Ala Phe Gly Pro Gly Thr Lys Leu Asp Ile Lys Arg Thr Val
            115                 120                 125

Ala Ala Pro Ser Val Phe Ile Phe Pro Pro Ser Asp Glu Gln Leu Lys
            130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230
```

<210> SEQ ID NO 9
<211> LENGTH: 375
<212> TYPE: DNA
<213> ORGANISM: Artificial Sequence
<220> FEATURE:
<223> OTHER INFORMATION: Nucleotide sequence encoding the variable part
      of the heavy chain

<400> SEQUENCE: 9
caggtgcagc tgcaggaatc tggccctggc ctgctgaagc ccagcgagac actgtctctg        60
acctgcgccg tgtccggcga ctctatcagc ggcggctact actggtcttg gatcaggcag       120
agccccggca agggcctgga atggatcggc ctgatctacg gcagcaccgc cgacaccaga       180
tacaacccca gcctgaaggg cagagtgacc atcagcaagg acaccagcaa gaaccagctg       240
tctctgcagc tgagaagcgt gaccgctgcc gacaccgccg tgtactactg tgccagaagc       300
ggctacaact tttggagcgg cgagtactac ggcctggact cttggggaca gggcgctgtc       360
gtgacagtgt ccagc                                                        375

<210> SEQ ID NO 10
<211> LENGTH: 321
<212> TYPE: DNA
<213> ORGANISM: Artificial Sequence
<220> FEATURE:
<223> OTHER INFORMATION: Nucleotide sequence encoding the variable part
      of the light chain

<400> SEQUENCE: 10
gccatccagc tgacccagag ccctagctct ctgagcgcct acgtgggcga caaagtgacc        60
atcacctgtc acgccagcca gggcatcaac agctggctgg cctggtatca gcagaagccc       120
ggcaaggccc ccaagctgct gatctacaag gccagcagcc tgctgagcgg cgtgcccagc       180
agattcagcg gctctggctc tggcaccgac tacaccctga ccatcagctc cctgcagagc       240
gaggacttcg ccagctacta ctgcctgcag tacgacagcc ccctctggc cttcggccct        300 ggaacaaagc tggacatcaa g                                                 321

<210> SEQ ID NO 11
<211> LENGTH: 990
<212> TYPE: DNA
<213> ORGANISM: Artificial Sequence
<220> FEATURE:
<223> OTHER INFORMATION: Nucleotide sequence encoding the constant part
      of the heavy chain

<400> SEQUENCE: 11
gcctctacca agggcccaag cgtgttccct ctggccccta gcagcaagtc tacctctggc        60
ggaacagccg ccctgggctg cctcgtgaag gactactttc ccgagcccgt gaccgtgtcc       120
tggaactctg gcgctctgac aagcggcgtg cacaccttcc ctgccgtgct gcagtctagc       180
ggcctgtaca gcctgagcag cgtcgtgact gtgccctcta gctctctggg cacccagacc       240
tacatctgca acgtgaacca caagcccagc aacaccaagg tggacaagaa ggtggaaccc       300
aagagctgcg acaagaccca cacctgtcct ccctgtcctg ccctgaact gctgggcgga       360 ccttccgtgt tcctgttccc cccaaagcct aaggacaccc tgatgatcag caggacccccc      420 gaagtgacct gcgtggtggt ggatgtgtcc cacgaggacc ctgaagtgaa gttcaattgg       480
tacgtggacg gcgtggaagt gcacaacgcc aagaccaagc ctagagagga acagtacaac       540
agcacctaca gggtggtgtc tgtgctgaca gtgctgcacc aggactggct gaacggcaaa       600

```
gagtacaagt gcaaggtgtc aacaaggcc ctgccagccc ccatcgaaaa gaccatctcc    660
aaggccaagg gacagcctcg cgagcccag gtgtacacac tgcctcccag cagggacgag    720
ctgacaaaga atcaggtgtc cctgacctgt ctcgtgaaag gcttctaccc agcgacatt    780 gccgtggaat gggagagcaa cggccagccc gagaacaact acaagaccac ccccctgtg    840 ctggacagcg acggctcatt cttcctgtac tccaagctga ccgtggacaa gtccaggtgg    900
cagcagggca acgtgttcag ctgctccgtg atgcacgagg ccctgcacaa ccactacacc    960
cagaagtccc tgagcctgag ccctggcaag                                     990

<210> SEQ ID NO 12
<211> LENGTH: 321
<212> TYPE: DNA
<213> ORGANISM: Artificial Sequence
<220> FEATURE:
<223> OTHER INFORMATION: Nucleotide sequence encoding the constant part
      of the light chain

<400> SEQUENCE: 12
aggaccgtgg ccgcaccaag tgtctttatc ttcccaccca gcgacgagca gctgaagtcc    60
ggcacagctt ccgtcgtgtg cctgctgaac aacttctacc ctagggaagc caaggtgcag    120
tggaaggtgg acaacgccct gcagtccggc aactcccagg aaagcgtgac cgagcaggac    180
agcaaggact ccacctacag cctgagcagc accctgacac tgagcaaggc cgactacgag    240
aaacataagg tgtacgcctg cgaagtgacc caccagggcc tgtctagccc cgtgaccaag    300
agcttcaaca ggggcgagtg c                                              321

<210> SEQ ID NO 13
<211> LENGTH: 1365
<212> TYPE: DNA
<213> ORGANISM: Artificial Sequence
<220> FEATURE:
<223> OTHER INFORMATION: Nucleotide sequence encoding the heavy chain

<400> SEQUENCE: 13
caggtgcagc tgcaggaatc tggccctggc ctgctgaagc ccagcgagac actgtctctg    60
acctgcgccg tgtccggcga ctctatcagc ggcggctact actggtcttg gatcaggcag    120
agccccggca agggcctgga atggatcggc ctgatctacg gcagcaccgc cgacaccaga    180 tacaaccca gcctgaaggg cagagtgacc atcagcaagg acaccagcaa gaaccagctg    240
tctctgcagc tgagaagcgt gaccgctgcc gacaccgccg tgtactactg tgccagaagc    300
ggctacaact tttggagcgg cgagtactac ggcctggact cttggggaca gggcgctgtc    360
gtgacagtgt ccagcgcctc taccaagggc ccaagcgtgt ccctctggc ccctagcagc    420 aagtctacct ctgggcggaac agccgccctg ggctgcctcg tgaaggacta ctttcccgag    480
cccgtgaccg tgtcctggaa ctctggcgct ctgacaagcg gcgtgcacac cttccctgcc    540
gtgctgcagt ctagcggcct gtacagcctg agcagcgtcg tgactgtgcc ctctagctct    600
ctgggcaccc agacctacat ctgcaacgtg aaccacaagc ccagcaacac caaggtggac    660
aagaaggtgg aacccaagag ctgcgacaag acccacacct gtcctccctg tcctgccct    720 gaactgctgg gcggaccttc cgtgttcctg ttcccccaa gcctaagga caccctgatg    780 atcagcagga cccccgaagt gacctgcgtg gtggtggatg tgtcccacga ggaccctgaa    840
gtgaagttca attggtacgt ggacggcgtg gaagtgcaca acgccaagac caagcctaga    900
gaggaacagt acaacagcac ctacagggtg gtgtctgtgc tgacagtgct gcaccaggac    960
```

```
tggctgaacg gcaaagagta caagtgcaag gtgtccaaca aggccctgcc agccccatc    1020 gaaaagacca tctccaaggc caagggacag cctcgcgagc ccaggtgta cacactgcct    1080 cccagcaggg acgagctgac aaagaatcag gtgtccctga cctgtctcgt gaaaggcttc   1140
taccccagca cattgccgt ggaatgggag agcaacggcc agcccgagaa caactacaag    1200 accaccccc ctgtgctgga cagcgacggc tcattcttcc tgtactccaa gctgaccgtg    1260
gacaagtcca ggtggcagca gggcaacgtg ttcagctgct ccgtgatgca cgaggccctg   1320
cacaaccact acacccagaa gtccctgagc ctgagccctg gcaag                  1365

<210> SEQ ID NO 14
<211> LENGTH: 642
<212> TYPE: DNA
<213> ORGANISM: Artificial Sequence
<220> FEATURE:
<223> OTHER INFORMATION: Nucleotide sequence encoding the light chain

<400> SEQUENCE: 14
gccatccagc tgacccagag ccctagctct ctgagcgcct acgtgggcga caaagtgacc    60
atcacctgtc acgccagcca gggcatcaac agctggctgg cctggtatca gcagaagccc   120
ggcaaggccc ccaagctgct gatctacaag gccagcagcc tgctgagcgg cgtgcccagc   180
agattcagcg gctctggctc tggcaccgac tacaccctga ccatcagctc cctgcagagc   240
gaggacttcg ccagctacta ctgcctgcag tacgacagcg cccctctggc cttcggccct   300
ggaacaaagc tggacatcaa ggaggaccgtg gccgcaccaa gtgtctttat cttcccaccc   360
agcgacgagc agctgaagtc cggcacagct tccgtcgtgt gcctgctgaa caacttctac   420
cctagggaag ccaaggtgca gtggaaggtg gacaacgccc tgcagtccgg caactcccag    480
gaaagcgtga ccgagcagga cagcaaggac tccacctaca gcctgagcag caccctgaca    540
ctgagcaagg ccgactacga gaaacataag gtgtacgcct gcgaagtgac ccaccagggc    600
ctgtctagcc ccgtgaccaa gagcttcaac aggggcgagt gc                      642

<210> SEQ ID NO 15
<211> LENGTH: 1419
<212> TYPE: DNA
<213> ORGANISM: Artificial Sequence
<220> FEATURE:
<223> OTHER INFORMATION: Nucleotide encoding the heavy chain comprising
      an N-terminal signal peptide

<400> SEQUENCE: 15
atgcgatggt cctggatctt cctgctgctg ctgagcatca ccagcgccaa cgctcaggtg    60
cagctgcagg aatctggccc tggcctgctg aagcccagcg agacactgtc tctgacctgc   120
gccgtgtccg gcgactctat cagcggcggc tactactggt cttggatcag gcagagcccc   180
ggcaagggcc tggaatggat cggcctgatc tacggcagca ccgccgacac cagatacaac   240
cccagcctga aggcagagt gaccatcagc aaggacacca gcaagaacca gtgtctctg     300 cagctgagaa gcgtgaccgc tgccgacacc gccgtgtact actgtgccag aagcggctac    360
aacttttgga gcggcgagta ctacggcctg gactcttggg gacagggcgc tgtcgtgaca    420
gtgtccagcg cctctaccaa gggcccaagc gtgttccctc tggccccta cagcaagtct    480 acctctgggcg gaacagccgc cctgggctgc ctcgtgaagg actactttcc cgagcccgtg   540
accgtgtcct ggaactctgg cgctctgaca agcggcgtgc acaccttccc tgccgtgctg   600
cagtctagcg gcctgtacag cctgagcagc gtcgtgactg tgccctctag ctctctgggc   660
```

```
acccagacct acatctgcaa cgtgaaccac aagcccagca acaccaaggt ggacaagaag    720
gtggaaccca agagctgcga caagaccac acctgtcctc cctgtcctgc ccctgaactg    780
ctgggcggac cttccgtgtt cctgttcccc ccaaagccta aggacaccct gatgatcagc    840 aggaccccg aagtgacctg cgtggtggtg gatgtgtccc acgaggaccc tgaagtgaag    900
ttcaattggt acgtggacgg cgtggaagtg cacaacgcca agaccaagcc tagagaggaa    960
cagtacaaca gcacctacag ggtggtgtct gtgctgacag tgctgcacca ggactggctg   1020
aacggcaaag agtacaagtg caaggtgtcc aacaaggccc tgccagcccc catcgaaaag   1080
accatctcca aggccaaggg acagcctcgc gagcccagg tgtacacact gcctcccagc    1140
agggacgagc tgacaaagaa tcaggtgtcc ctgacctgtc tcgtgaaagg cttctacccc   1200
agcgacattg ccgtggaatg ggagagcaac ggccagcccg agaacaacta caagaccacc   1260
ccccctgtgc tggacagcga cggctcattc ttcctgtact ccaagctgac cgtggacaag   1320
tccaggtggc agcagggcaa cgtgttcagc tgctccgtga tgcacgaggc cctgcacaac   1380
cactacaccc agaagtccct gagcctgagc cctggcaag                          1419
```

<210> SEQ ID NO 16  
<211> LENGTH: 696  
<212> TYPE: DNA  
<213> ORGANISM: Artificial Sequence  
<220> FEATURE:  
<223> OTHER INFORMATION: Nucleotide sequence encoding the light chain  
      comprising an N terminal signal peptide

<400> SEQUENCE: 16

```
atgcgatggt cctggatctt cctgctgctg ctgagcatca ccagcgccaa cgccgccatc     60
cagctgaccc agagccctag ctctctgagc gcctacgtgg gcgacaaagt gaccatcacc    120
tgtcacgcca gccagggcat caacagctgg ctggcctggt atcagcagaa gcccggcaag    180
gcccccaagc tgctgatcta caaggccagc agcctgctga gcggcgtgcc cagcagattc    240
agcggctctg gctctggcac cgactacacc ctgaccatca gctccctgca gagcgaggac    300
ttcgccagct actactgcct gcagtacgac agcgcccctc tggccttcgg ccctggaaca    360
aagctggaca tcaagaggac cgtggccgca ccaagtgtct ttatcttccc acccagcgac    420
gagcagctga gtccggcac agcttccgtc gtgtgcctgc tgaacaactt ctaccctagg    480
gaagccaagg tgcagtggaa ggtggacaac gccctgcagt ccggcaactc ccaggaaagc    540
gtgaccgagc aggacagcaa ggactccacc tacagcctga gcagcaccct gacactgagc    600
aaggccgact acgagaaaca taaggtgtac gcctgcgaag tgacccacca gggcctgtct    660
agccccgtga ccaagagctt caacagggc gagtgc                                696
```

<210> SEQ ID NO 17  
<211> LENGTH: 1448  
<212> TYPE: DNA  
<213> ORGANISM: Artificial Sequence  
<220> FEATURE:  
<223> OTHER INFORMATION: Nucleotide sequence encoding the heavy chain as  
      synthesized

<400> SEQUENCE: 17

```
gctagcgccg ccaccatgcg atggtcctgg atcttcctgc tgctgctgag catcaccagc     60
gccaacgctc aggtgcagct gcaggaatct ggccctggcc tgctgaagcc cagcgagaca    120
ctgtctctga cctgcgccgt gtccggcgac tctatcagcg gcggctacta ctggtcttgg    180
```

```
atcaggcaga gccccggcaa gggcctggaa tggatcggcc tgatctacgg cagcaccgcc    240
gacaccagat acaaccccag cctgaagggc agagtgacca tcagcaagga caccagcaag    300
aaccagctgt ctctgcagct gagaagcgtg accgctgccg acaccgccgt gtactactgt    360
gccagaagcg gctacaactt ttggagcggc gagtactacg gcctggactc ttggggacag    420
ggcgctgtcg tgacagtgtc cagcgcctct accaagggcc caagcgtgtt ccctctggcc    480
cctagcagca gtctacctc tggcggaaca gccgccctgg gctgcctcgt gaaggactac    540
tttcccgagc ccgtgaccgt gtcctggaac tctggcgctc tgacaagcgg cgtgcacacc    600
ttccctgccg tgctgcagtc tagcggcctg tacagcctga gcagcgtcgt gactgtgccc    660
tctagctctc tgggcaccca gacctacatc tgcaacgtga accacaagcc cagcaacacc    720
aaggtggaca gaaggtggaa cccaagagc tgcgacaaga cccacacctg tcctcccgtg    780
cctgcccctg aactgctggg cggaccttcc gtgttcctgt tccccccaaa gcctaaggac    840
accctgatga tcagcaggac ccccgaagtg acctgcgtgg tggtggatgt gtcccacgag    900
gaccctgaag tgaagttcaa ttggtacgtg gacggcgtga agtgcacaa cgccaagacc    960 aagcctagag aggaacagta caacagcacc tacagggtgg tgtctgtgct gacagtgctg   1020
caccaggact ggctgaacgg caaagagtac aagtgcaagg tgtccaacaa ggccctgcca   1080
gcccccatcg aaaagaccat ctccaaggcc aagggacagc ctcgcgagcc ccaggtgtac   1140
acactgcctc ccagcaggga cgagctgaca aagaatcagg tgtccctgac ctgtctcgtg   1200
aaaggcttct accccagcga cattgccgtg gaatgggaga gcaacggcca gcccgagaac   1260
aactacaaga ccacccccc tgtgctggac agcgacggct cattcttcct gtactccaag   1320
ctgaccgtgg acaagtccag gtggcagcag ggcaacgtgt tcagctgctc cgtgatgcac   1380
gaggccctgc acaaccacta cacccagaag tccctgagcc tgagccctgg caagtgatag   1440
ggcgcgcc                                                            1448

<210> SEQ ID NO 18
<211> LENGTH: 725
<212> TYPE: DNA
<213> ORGANISM: Artificial Sequence
<220> FEATURE:
<223> OTHER INFORMATION: Nucleotide sequence encoding the light chain as
      synthesized

<400> SEQUENCE: 18
actagtgccg ccaccatgcg atggtcctgg atcttcctgc tgctgctgag catcaccagc     60
gccaacgccg ccatccagct gacccagagc cctagctctc tgagcgccta cgtgggcgac    120
aaagtgacca tcacctgtca cgccagccag ggcatcaaca gctggctggc ctggtatcag    180
cagaagcccg gcaaggcccc caagctgctg atctacaagg ccagcagcct gctgagcggc    240
gtgcccagca gattcagcgg ctctggctct ggcaccgact acaccctgac catcagctcc    300
ctgcagagcc aggacttcgc cagctactac tgcctgcagt acgacagcgc cctctggcc    360 ttcggccctg gaacaaagct ggacatcaag aggaccgtgg ccgcaccaag tgtctttatc    420
ttcccaccca gcgacgagca gctgaagtcc ggcacagctt ccgtcgtgtg cctgctgaac    480
aacttctacc ctagggaagc caaggtgcag tggaaggtgg acaacgccct gcagtccggc    540
aactcccagg aaagcgtgac cgagcaggac agcaaggact ccacctacag cctgagcagc    600
accctgacac tgagcaaggc cgactacgag aaacataagg tgtacgcctg cgaagtgacc    660
caccagggcc tgtctagccc cgtgaccaag agcttcaaca ggggcgagtg ctagtgaact    720
```

```
ctaga                                                                         725

<210> SEQ ID NO 19
<211> LENGTH: 18
<212> TYPE: PRT
<213> ORGANISM: Artificial Sequence
<220> FEATURE:
<223> OTHER INFORMATION: Signal peptide

<400> SEQUENCE: 19

Met Arg Trp Ser Trp Ile Phe Leu Leu Leu Leu Ser Ile Thr Ser Ala
1               5                   10                  15

Asn Ala

<210> SEQ ID NO 20
<211> LENGTH: 53
<212> TYPE: DNA
<213> ORGANISM: Artificial Sequence
<220> FEATURE:
<223> OTHER INFORMATION: Sequence encoding the signal peptide

<400> SEQUENCE: 20
atgcgatggt cctggatctt cctgctgctg ctgagcatca ccagcgccaa cgc           53
```